(12) United States Patent  (10) Patent No.: US 7,752,000 B2
Schulze et al.  (45) Date of Patent: Jul. 6, 2010

(54) CALIBRATION OF NON-VIBRATING CONTACT POTENTIAL DIFFERENCE MEASUREMENTS TO DETECT SURFACE VARIATIONS THAT ARE PERPENDICULAR TO THE DIRECTION OF SENSOR MOTION

(75) Inventors: Mark A. Schulze, Austin, TX (US); William R. Usry, Austin, TX (US)

(73) Assignee: QCept Technologies, Inc., Atlanta, GA (US)

( * ) Notice: Subject to any disclaimer, the term of this patent is extended or adjusted under 35 U.S.C. 154(b) by 306 days.

(21) Appl. No.: 12/151,054

(22) Filed: May 2, 2008

(65) Prior Publication Data

US 2009/0276176 A1  Nov. 5, 2009

(51) Int. Cl.
  *G01D 21/00*  (2006.01)
(52) U.S. Cl. .............................. 702/85; 73/104; 73/105; 324/158.1
(58) Field of Classification Search .................. 702/85; 324/158.1; 73/104, 105
  See application file for complete search history.

(56) References Cited

U.S. PATENT DOCUMENTS

| | | | |
|---|---|---|---|
| 4,166,974 A | 9/1979 | Vermeers | |
| 4,295,092 A | 10/1981 | Okamura | |
| 4,481,616 A | 11/1984 | Matey | |
| 4,767,211 A | 8/1988 | Munakata et al. | |
| 4,973,910 A | 11/1990 | Wilson | |
| 5,087,533 A | 2/1992 | Brown | |
| 5,136,247 A | 8/1992 | Hansen | |
| 5,214,389 A | 5/1993 | Cao et al. | |
| 5,217,907 A | 6/1993 | Bulucea et al. | |
| 5,218,362 A | 6/1993 | Mayes et al. | |
| 5,270,664 A | 12/1993 | McMurtry et al. | |
| 5,272,443 A | 12/1993 | Winchip et al. | |
| 5,278,407 A | 1/1994 | Ikebe et al. | |
| 5,293,131 A | 3/1994 | Semones et al. | |
| 5,315,259 A | 5/1994 | Jostlein | |
| 5,369,370 A | 11/1994 | Stratmann et al. | |

(Continued)

FOREIGN PATENT DOCUMENTS

| | | |
|---|---|---|
| DE | 297 509 A5 | 1/1992 |
| EP | 1 039 277 | 9/2000 |
| EP | 1 304 463 B1 | 4/2003 |
| WO | WO 01/90730 A2 | 11/2001 |
| WO | WO 03/033993 A1 | 4/2003 |
| WO | WO 2004/070355 A2 | 8/2004 |

OTHER PUBLICATIONS

B Scruton and B.H. Blott, A High Resolution Probe for Scanning Electrostatic Potential Profiles Across Surfaces; Journal of Physics E: Scientific Instruments (May 1973), pp. 472-474; vol. 6, No. 5, Printed in Great Britain.

(Continued)

*Primary Examiner*—Drew A Dunn
*Assistant Examiner*—Hien X Vo
(74) *Attorney, Agent, or Firm*—Foley & Lardner LLP

(57) ABSTRACT

A method and system for determining the contact potential difference of a wafer surface using a non-vibrating contact potential difference probe and a vibrating contact potential difference probe. The method and system involves scanning the wafer surface with a non-vibrating contact potential difference sensor, integrating and scaling the resulting data, and applying offsets to individual tracks of data to match the integrated scaled data to measurements made using a vibrating contact potential difference sensor.

20 Claims, 27 Drawing Sheets

U.S. PATENT DOCUMENTS

| | | | |
|---|---|---|---|
| 5,381,101 | A | 1/1995 | Bloom et al. |
| 5,460,684 | A | 10/1995 | Saeki et al. |
| 5,517,123 | A | 5/1996 | Zhao et al. |
| 5,546,477 | A | 8/1996 | Knowles et al. |
| 5,583,443 | A | 12/1996 | McMurtry et al. |
| 5,723,980 | A | 3/1998 | Haase et al. |
| 5,723,981 | A | 3/1998 | Hellemans et al. |
| 5,773,989 | A | 6/1998 | Edelman et al. |
| 5,789,360 | A | 8/1998 | Song et al. |
| 5,974,869 | A | 11/1999 | Danyluk et al. |
| 5,977,788 | A | 11/1999 | Lagowski |
| 6,011,404 | A | 1/2000 | Ma et al. |
| 6,037,797 | A | 3/2000 | Lagowski et al. |
| 6,091,248 | A | 7/2000 | Hellemans et al. |
| 6,094,971 | A | 8/2000 | Edwards et al. |
| 6,097,196 | A | 8/2000 | Verkuil et al. |
| 6,114,865 | A | 9/2000 | Lagowski et al. |
| 6,127,289 | A | 10/2000 | Debusk |
| 6,139,759 | A | 10/2000 | Doezema et al. |
| 6,198,300 | B1 | 3/2001 | Doezema et al. |
| 6,201,401 | B1 | 3/2001 | Hellemans et al. |
| 6,232,134 | B1 | 5/2001 | Farber et al. |
| 6,255,128 | B1 | 7/2001 | Chacon et al. |
| 6,265,890 | B1 | 7/2001 | Chacon et al. |
| 6,517,669 | B2 | 2/2003 | Chapman |
| 6,520,839 | B1 | 2/2003 | Gonzalez-Martin et al. |
| 6,538,462 | B1 | 3/2003 | Lagowski et al. |
| 6,546,814 | B1 | 4/2003 | Choe et al. |
| 6,551,972 | B1 | 4/2003 | Lei et al. |
| 6,597,193 | B2 | 7/2003 | Lagowski et al. |
| 6,664,546 | B1 | 12/2003 | McCord et al. |
| 6,664,800 | B2 | 12/2003 | Chacon et al. |
| 6,679,117 | B2 | 1/2004 | Danyluk et al. |
| 6,680,621 | B2 | 1/2004 | Savtchouk et al. |
| 6,711,952 | B2 | 3/2004 | Leamy et al. |
| 6,717,413 | B1 | 4/2004 | Danyluk et al. |
| 6,771,091 | B2 | 8/2004 | Lagowski et al. |
| 6,791,310 | B2 | 9/2004 | Smith |
| 6,803,241 | B2 | 10/2004 | Eom et al. |
| 6,849,505 | B2 | 2/2005 | Lee et al. |
| 6,858,089 | B2 | 2/2005 | Castrucci |
| 6,929,531 | B2 | 8/2005 | Gotkis et al. |
| 6,982,567 | B2 | 1/2006 | Smith |
| 7,019,654 | B2 | 3/2006 | Danyluk et al. |
| 7,084,661 | B2 | 8/2006 | Thompson et al. |
| 7,107,158 | B2 | 9/2006 | Steele et al. |
| 7,153,476 | B2 | 12/2006 | Liu et al. |
| RE39,803 | E | 9/2007 | Danyluk et al. |
| 2002/0084253 | A1 | 7/2002 | Chapman |
| 2003/0139838 | A1 | 7/2003 | Marella |
| 2003/0164942 | A1 | 9/2003 | Take |
| 2003/0175945 | A1 | 9/2003 | Thompson et al. |
| 2004/0029131 | A1 | 2/2004 | Thompson et al. |
| 2004/0057497 | A1 | 3/2004 | Lagowski et al. |
| 2004/0058620 | A1 | 3/2004 | Gotkis et al. |
| 2004/0070355 | A1 | 4/2004 | Ogura |
| 2004/0105093 | A1 | 6/2004 | Hamamatsu et al. |
| 2004/0134515 | A1 | 7/2004 | Castrucci |
| 2004/0152250 | A1 | 8/2004 | Steele et al. |
| 2004/0241890 | A1 | 12/2004 | Steele et al. |
| 2005/0162178 | A1 | 7/2005 | Steele et al. |
| 2007/0010954 | A1 | 1/2007 | Steele et al. |

OTHER PUBLICATIONS

Yano D et al: "Nonvibrating contact potential difference probe measurement of a nanometer-scale lubricant on a hard disk", Journal of Tribology, American Society of Mechanical Engineers, New York, NY, US; vol. 121, No. 4, Oct. 1999, pp. 980-983, XP008031092, ISSN: 0742-4787 (pp. 980-981, fig. 4, first ref. on p. 983).

Castaldini A et al: "Surface analyses of polycrystalline and Cz-Si wafers", Solar Energy Materials and Solar Cells, Elsevier Science Publishers, Amsterdam, NL; vol. 72, No. 1-4, Apr. 2002, pp. 425-432, XP004339790, ISSN: 0927-0248 (whole document).

Korach C S et al: "Measurement of perfluoropolyether lubricant thickness on a magnetic disk surface", Applied Physics Letters, American Institute of Physics, New York, NY, US; vol. 79, No. 5, Jul. 30, 2001, pp. 698-700, XP012029958, ISSN: 0003-6951 (p. 699, left col.; fig. 2).

Yang Y et al: "Kelvin probe study on the perfluoropolyether film on metals", Tribology Letters, 2001, Kluwer Academic/Plenum Publishers, USA, vol. 10, No. 4, pp. 211-216, XP009035197, ISSN: 1023-8883 (p. 211-p. 212).

Castaldini A et al: "Scanning Kelvin probe and surface photovoltage analysis of multicrystalline silicon", Materials Science and Engineering B., Elsevier Sequoia, Lausanne, CH; vol. 91-92, Apr. 30, 2002, pp. 234-238, XP004355534, ISSN: 0921-5107 (chapters "2.2 Scanning Kelvin probe: and 4.2 Scanning Kelvin probe analyses").

Lagel B et al: "A novel detection system for defects and chemical contamination in semiconductors based upon the scanning Kelvin probe", $14^{th}$ International Vacuum Congress (IVC-14). $10^{th}$ International Conference on Solid Surfaces (ICS-10). $5^{th}$ International Conference on Nanometre-Scale Science and Technology (NANO-5). $10^{th}$ International Conference on Quantitative Surface Analysis; vol. 433-435, pp. 622-626, XP002292441, Surface Science, Aug. 2, 1999, Elsevier, NL, ISSN: 003906028 (whole document).

Ren J et al: "Scanning Kelvin Microscope: a new method for surface investigations" 8. Arbeitstatgung Angewandte Oberflachenanalytik 'AOFA 8' ('Applied Surface Analysis'), Kaiserslautern, DE, Sep. 5-8, 1994; vol. 353, No. 3-4, pp. 303-306, XP009035181, Fresenius' Jounal of Analytical Chemistry, Oct. 1995, Springer-Verlag, DE, ISSN: 0937-0633 (p. 304, right col.; fig. 1).

Baumgartner H et al: "Micro Kelvin probe for local work-function measurements", Review of Scientific Instrumetns, May 1988, USA; vol. 59, No. 5, pp. 802-805, XP0022922442, ISSN: 0034-6748 (abstract; fig. 4, chapter "V. Results").

Danyluk S: "Non-vibrating contact potential imaging for semiconductor fabrication", Semicon West 2003, 'Online!, Jul. 14, 2003, pp. 1-15, XP002292443, 'retrieved from the internet: ,URL:http://dom.semi.org/web/wFiles.nsf/Lookup/TIS18_QceptTechnologiesInc/$file/TIS18%20QceptTechnologiesInc.Alternate.pdf. retrieved on Aug. 13, 2004 (whole document).

Moorman, M. et al., "A Novel, Micro-Contact Potential Difference Probe," Sensors and Actuators B, Elsevier Sequoia S.A., Lausanne, CH, vol. 94, No. 1. Jan. 27, 2003.

Reid, Jr., Lennox Errol, "Surface Characterization of Hard Disks Using Non-Contact Work Function Capacitance Probe," A Thesis Presented to the Academic Faculty in Partial Fulfillment of the Requirements for the Degree of Master of Science in Mechanical Engineering, Georgia Institute of Technology, Jun. 1986.

PCT International Search Report for PCT/US2009/041948 dated Nov. 25, 2009, 3 pages.

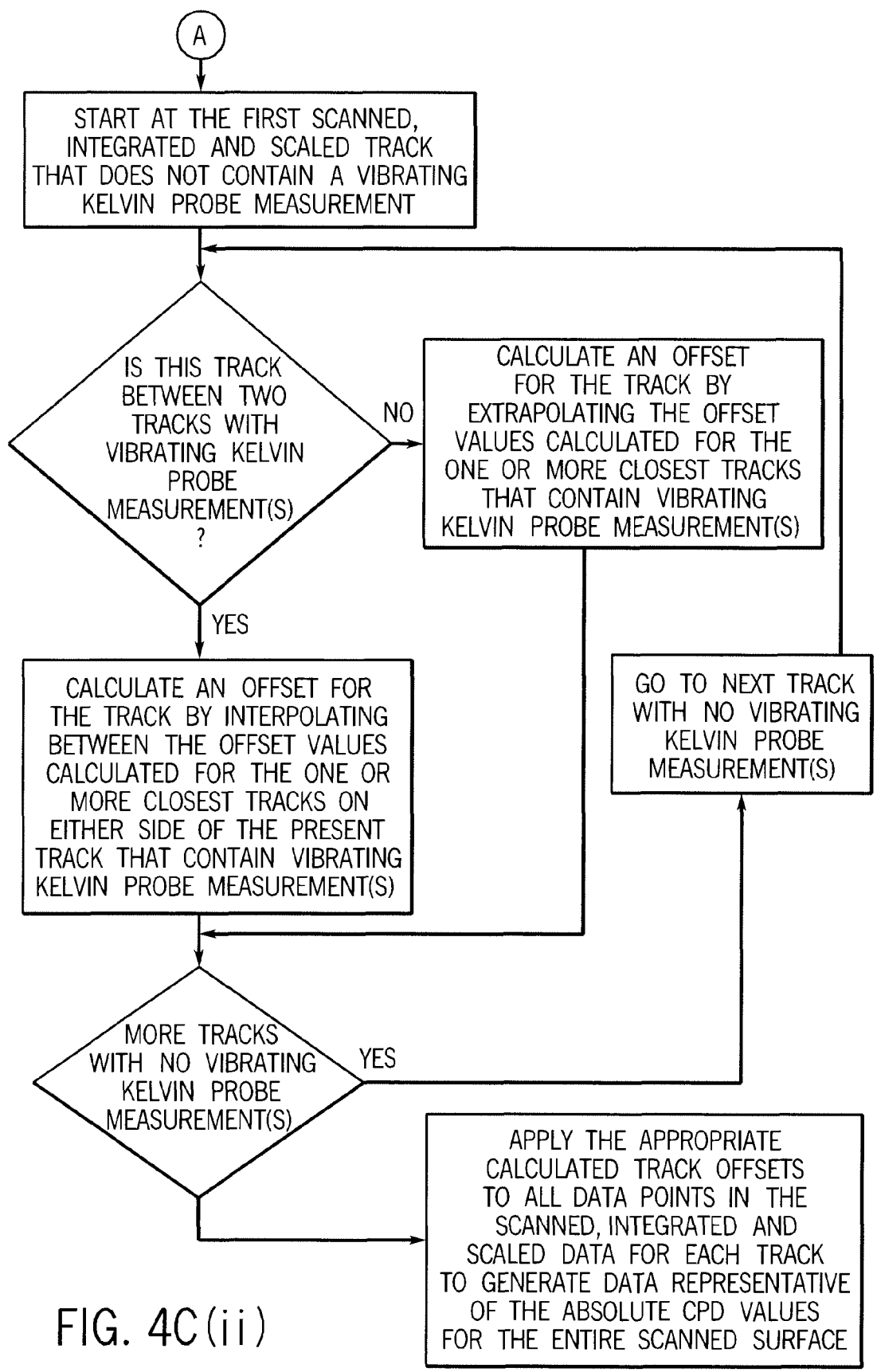
FIG. 4C(ii)

CALIBRATION OF NON-VIBRATING CONTACT POTENTIAL DIFFERENCE MEASUREMENTS TO DETECT SURFACE VARIATIONS THAT ARE PERPENDICULAR TO THE DIRECTION OF SENSOR MOTION

The present invention is directed to methods and systems for the inspection of surfaces and materials, including semiconductor surfaces and semiconductor materials. More particularly, the present invention is directed to methods for detecting and measuring surface or subsurface non-uniformities and/or charges using contact potential difference sensors in both vibrating and non-vibrating modes so as to establish the presence of any non-uniformities with precision over the entire surface.

BACKGROUND OF THE INVENTION

The function, reliability and performance of semiconductor devices depend on the use of semiconductor materials and surfaces which are clean and uniform. Billions of dollars and countless man-hours have been spent developing, characterizing, and optimizing systems and processes for fabricating and processing semiconductor materials. A primary goal of this activity has been the fabrication of materials and surfaces that are extremely clean and that have predetermined and desired properties that are uniform, or vary uniformly, across the entire wafer. In order to characterize and optimize these processes and the resulting material, it is necessary to be able to inspect and measure surface or bulk cleanliness and uniformity. For real-time process control, it is necessary to be able to make many measurements across a surface at high speed, and to do so in a manner that does not damage or contaminate the semiconductor surface.

One method of inspecting and measuring surfaces utilizes a non-vibrating contact potential difference sensor. The non-vibrating contact potential difference sensor consists of a conductive probe that is positioned close to a surface, and is electrically connected to the surface. The probe and the surface form a capacitor. An electrical potential is formed between the probe tip and the surface due to the difference in work functions or surface potentials of the two materials. This electrical potential is called the contact potential difference, or surface potential difference, between the two surfaces. The probe tip is translated parallel to the surface, or the surface is translated beneath the probe. Changes in the work function or surface potential at different points on the surface result in changes in contact potential difference between the surface and the probe tip. These changes in electrical potential cause an electrical current to flow in or out of the sensor probe tip. This current is amplified, converted to a voltage, and sampled to form a continuous stream of data which represents changes in potential across the measured surface. The non-vibrating contact potential difference sensor can provide a continuous stream of data at rates greater than 100,000 samples per second. High data acquisition rates permit high-resolution images of whole semiconductor wafers to be acquired in only a few minutes.

The non-vibrating contact potential difference sensor produces a signal that is a combination of two characteristics of the measured surface—changes in work function and changes in surface height. The charge on the probe tip is determined as follows:

$$Q = CV \tag{1}$$

Where Q is the charge on the probe tip, C is the capacitance between the probe tip and the measured surface, and V is the contact potential difference between the probe tip and the surface.

The current, i, into the probe tip is the derivative of the charge on the probe tip and is given by the following formula:

$$i = \frac{dQ}{dt} = C\frac{dV}{dt} + V\frac{dC}{dt} \tag{2}$$

The current, i, is the sum of two terms: the dV/dt term and the dC/dt term. The dV/dt term represents changes in the voltage between the probe tip and the wafer surface, and the dC/dt term represents changes in the capacitance between the probe tip and the wafer surface. The potential of the probe tip is fixed during the scanning operation, so changes in the dV/dt term arise due to changes in the potential across the measured surface. Changes in the dC/dt term result from changes in the distance between the probe tip and the wafer surface, which most often result from changes in the height of the wafer surface. In most wafer surface scanning applications, the signal from capacitance changes is minimized by controlling the height of the probe tip above the wafer surface, minimizing wafer surface height variations, and/or minimizing the average voltage between the probe tip and the wafer surface through the application of a DC bias voltage. As a result, the capacitance signal is negligible and can be disregarded.

An important characteristic of the non-vibrating contact potential difference sensor is that it produces data that is differential; which means that it generates data that represents differences, or changes, in surface potential or work function across the measured surface. The output of the sensor represents changes in surface potential in the direction of travel of the sensor probe tip relative to the surface. The sensor output does not include any data on the change in surface potential in the direction perpendicular, or orthogonal, to the direction of travel of the sensor probe tip. Also, the sensor output does not provide data on the absolute contact potential difference between the probe tip and measured surface at any point. The sensor output only contains information on changes in surface potential.

The non-vibrating contact potential difference sensor relies on relative motion between the probe tip and measured surface to generate a signal. The act of moving the sensor probe tip parallel to the wafer surface to generate a signal is called scanning. There are numerous options for generating scanning motion between the probe tip and a wafer surface. For example, the wafer can be held fixed and the probe tip can be moved back-and-forth above the wafer surface to generate linear "tracks" of data, where a track is a continuous series of sequential data samples. Multiple linear tracks can be assembled into an image of the scanned surface. Alternatively, the probe can be held fixed and the wafer moved back-and-forth beneath the sensor probe tip. This type of scanning, where either the sensor or wafer is moved back-and-forth to produce a series of parallel linear scans, is often called raster scanning. Another option for generating the scanning motion is to rotate the wafer beneath the sensor probe tip, and move the sensor or wafer along a radius of the wafer to acquire a series of concentric circular tracks at different radii from the wafer center. These concentric tracks can then be assembled into an image of the scanned surface. This type of scanning operation is often called radial scanning because the probe tip is moved along a radius of the wafer.

With radial scanning, the spinning motion of the wafer provides relative motion between the probe tip and measured surface without the high accelerations and decelerations required by a raster scanning operation. Raster scanning requires accelerating the probe or wafer to the required scanning speed, acquiring a single track of data, and then decelerating and re-accelerating the probe or wafer in the opposite direction. With radial scanning, the wafer can be spun at a fixed or slowly varying speed, and the sensor can be moved small distances with low accelerations from one radial track to the next. As a result, the wafer surface can be scanned in a much shorter period of time with much less vibration and lower power consumption than with raster scanning.

The differential nature of the non-vibrating contact potential difference sensor signal means that a signal is generated only when the probe moves across a portion of the wafer surface where the surface potential changes from one location to another. If the sensor moves from an area with one surface potential value to an area with another surface potential value, a signal is generated only at the transition (edge) between the two regions. The differential sensor signal is proportional to the change in surface potential along the direction of motion of the probe. However, this differential signal can be converted to a new signal which is a linear function of relative surface potential by integrating the sensor signal. Integration is accomplished by computing the cumulative sum of consecutive samples. The integrated signal provides information on relative surface potentials in the direction of motion of the probe, but does not provide any information about surface variations perpendicular to the direction of motion, nor does it provide a measure of the absolute value of the contact potential difference. As a result of the scanning motion, any orthogonal variation is undetectable in the absence of additional measurements for determining that variation. In the case of raster-scanning, data on orthogonal variations can be acquired by performing the scanning operation twice: once in each of two perpendicular directions. However, this operation requires two scans of the surface, which doubles the scanning time. In the case of radial scanning, the scanning mechanics do not easily lend themselves to scanning each point on the wafer surface in two orthogonal directions. As a result, the circular motion of the probe relative to the wafer surface is not effective in detecting surface non-uniformities that vary radially. These types of radial variations in contact potential difference can arise from a variety of wafer processing steps. For example, dielectric charging caused by single wafer cleans or plasma processing operations can create a radial charge pattern that cannot be detected by the non-vibrating contact potential difference sensor using the radial scanning method.

As mentioned above, the non-vibrating contact potential difference sensor produces differential data that can be integrated to produce data representative of relative contact potential difference values across the surface. It is also possible to calibrate integrated non-vibrating contact potential difference data using vibrating contact potential difference measurements. Vibrating contact potential difference sensors are often called Kelvin probes, or Kelvin-Zisman probes. This type of sensor produces measurements of the absolute contact potential difference, in volts, between the probe tip and a particular point on the measured surface. Vibrating contact potential difference measurements, however, are very slow compared to non-vibrating contact potential difference measurements, and this technique is not suited to full-wafer imaging at production speeds. Integrated non-vibrating contact potential difference measurements can be transformed to provide absolute contact potential difference values by calculating a linear transformation between Kelvin probe measurements at multiple points and the integrated non-vibrating contact potential difference values at the same points on the measured surface. The best-fit linear transformation can be calculated using a technique such as least-squares line fitting. Once the best-fit linear transformation is calculated, it is applied to all points in the integrated non-vibrating contact potential difference image. This technique provides approximations of the absolute contact potential difference values for all scanned points, and is much faster than measuring the entire wafer surface using a vibrating contact potential difference sensor. The integrated non-vibrating data, however, still does not include any information on variations in surface potential perpendicular to the direction of motion of the probe tip. As a result, the integrated and transformed data will not include information on variations in surface potential that are perpendicular to the direction of motion of the scanning probe, and the resulting data will be incorrect if there are significant surface potential changes in this direction. This type of orthogonal variation in surface potential is common for radially scanned wafers because, as noted above, significant radial variations in surface potential can result from common semiconductor manufacturing processes. If significant radial variations exist, the correlation coefficient between the vibrating Kelvin probe measurements and the integrated radially-scanned non-vibrating contact potential difference data will be low, because the integrated non-vibrating contact potential difference image will not include this significant radial variation in surface potential.

SUMMARY OF THE INVENTION

The system and methods described in this invention provide an enhanced application of a combined vibrating and non-vibrating contact potential difference inspection system that allows the rapid imaging of surfaces and the detection of surface potential non-uniformities in both the direction of motion of the non-vibrating (scanning) probe and perpendicular to the direction of motion of the non-vibrating probe. This capability is particularly useful for the detection of radial non-uniformities on surfaces scanned with a non-vibrating probe using a radial scanning system. Hereinafter, material susceptible to inspection by the system herein described will be denoted generally as a "wafer". In preferred applications, such as for evaluation of conventional silicon single crystal wafers, various examples are described hereinafter for four different wafers subjected to different processing conditions. The invention includes both a vibrating and a non-vibrating contact potential difference measurement capability. The vibrating contact potential difference measurement capability provides data on the absolute contact potential difference between the probe tip and various points on the wafer surface, while the non-vibrating contact potential difference measurement capability provides data on changes in the contact potential difference across the wafer surface. This apparatus consists of a correlated system of a sensor or sensors capable of both vibrating and non-vibrating contact potential difference measurements, a system for mechanically fixturing the wafer, a system for positioning the sensor a fixed distance above the wafer surface and generating relative motion between the probe tip and wafer surface such that the sensor probe tip moves parallel to the wafer surface, a system for applying a bias voltage to either the sensor probe tip or the wafer surface, a system for vibrating the sensor probe tip perpendicular to the wafer surface, and a system for acquiring and processing the output signal from the sensor or sensors to identify and classify wafer non-uniformities.

The system further includes the ability to apply a bias voltage to either the sensor probe tip or the wafer surface to modify the electrical potential between the probe tip and wafer. In this case the dC/dt term in Equation (2) includes a bias voltage as shown in the following formula:

$$i = C\frac{dV}{dt} + (V_{CPD} + V_{bias})\frac{dC}{dt} \quad (3)$$

In Equation (3), VCPD is the voltage between the probe tip and wafer surface that results solely from electrically connecting the probe tip and the wafer surface. This voltage is called the surface potential difference or contact potential difference, often abbreviated as CPD. Vbias is an additional voltage that is applied to the probe tip or wafer by the inspection system to facilitate detection and classification of wafer non-uniformities. If Vbias is constant during the scanning operation, then it does not affect the dV/dt term because dVbias/dt=0.

The system also includes a mechanism for positioning the sensor above a point on the wafer and vibrating the sensor perpendicular to the wafer surface while the bias voltage is adjusted. Vibrating the probe tip perpendicular to the wafer surface causes changes in the capacitance between the probe tip and the wafer surface, which results in a signal due to the VdC/dt term in Equations (2) and (3). This signal is proportional to the contact potential difference (V) between the probe tip and the wafer surface. The variable bias voltage is added to the contact potential difference and modifies the voltage between the probe tip and wafer surface. The bias voltage is adjusted and the bias voltage that causes the vibrating sensor signal to go to zero is determined. This voltage is the negative of the contact potential difference between the probe tip and wafer surface. After adjusting the bias voltage and determining the voltage that results in zero signal from the vibrating probe, the contact potential difference is calculated from this bias voltage. This type of system for measuring contact potential difference is known as a vibrating Kelvin probe or Kelvin-Zisman probe.

The invention also includes a system and methods for processing the resulting data to detect and discriminate between different types of surface non-uniformities based on the data generated by both vibrating and non-vibrating contact potential difference sensors.

The non-vibrating contact potential difference sensor can acquire data relatively quickly, so that whole-wafer images of changes in surface potential can be acquired in only a few minutes. The vibrating contact potential difference sensor provides a measurement of the absolute contact potential difference between the probe tip and the wafer, but is relatively slow. For example, the non-vibrating sensor can acquire over 100,000 samples per second, while the vibrating probe can acquire only a few samples per second at most. By combining the high-resolution non-vibrating contact potential difference images with the relatively slow, low-resolution vibrating sensor data, data on the absolute contact potential difference of the entire wafer surface can be obtained at speeds that are comparable to that of the non-vibrating sensor.

In order to convert the non-vibrating data to correspond to the actual contact potential difference at every point on the wafer surface, the non-vibrating contact potential difference data is first integrated. The simplest way to do this is to begin at the first sample acquired in each track and compute the cumulative sum at each succeeding sample in the track. Other methods for numerical integration may be used as well. The integrated data is proportional to changes in surface potential along the track. However, each integrated track of data must be multiplied by a scaling factor and then offset by a constant to obtain the correct absolute contact potential difference at each point. The appropriate scaling factor (slope) and offset (constant of integration) between the integrated data and the actual contact potential difference values at each point are unknown, but can be determined by measuring the actual contact potential difference at two or more points on the wafer surface using the vibrating Kelvin probe and then comparing the Kelvin probe values to the integrated non-vibrating contact potential difference measurements at the same points on the surface.

If the measured wafer has minimal surface potential variation perpendicular to the direction of motion of the scanning probe, then the integrated non-vibrating contact potential difference data can be approximated as a linear function of the actual contact potential difference values for the entire wafer surface. These data can be converted to match multiple vibrating contact potential difference measurements by mathematical algorithms.

In one preferred embodiment, vibrating measurements are taken at several locations across the wafer (a minimum of two locations). The linear function that best fits the vibrating contact potential difference measurements at multiple points to the integrated non-vibrating data at the same points on the wafer surface is calculated. This linear transformation is then applied to all of the integrated non-vibrating measurements. The resulting linear scaling of the integrated non-vibrating measurements provides an approximation of the contact potential difference value at each location on the wafer surface. However, the resulting image data does not include any information on contact potential difference variations that are perpendicular to the direction of motion of the non-vibrating probe. The resulting linear transformation consists of a scaling factor and an offset. The offset represents the mean absolute contact potential difference of the entire wafer surface. The scaling factor converts integrated non-vibrating contact potential difference sensor values into relative surface potential values. This scaling factor is characteristic of the sensor and scanning parameters used to acquire the non-vibrating contact potential difference data. Once this scaling factor has been determined for a particular sensor and scanning method, it can be applied to subsequent integrated non-vibrating contact potential difference data acquired using the same sensor and parameters to convert the integrated data into relative surface potential values. A scaling factor obtained by this method is used in the methods described below.

In another preferred embodiment of this invention, a wafer is scanned with a non-vibrating contact potential difference sensor, and the resulting data is integrated and multiplied by an appropriate scaling factor to convert the integrated data into relative surface potential values. The scaling factor is determined using the method described above. Multiple vibrating contact potential difference measurements are then taken along a line which is perpendicular to the direction of motion of the non-vibrating sensor. The scaled, integrated non-vibrating contact potential difference value at the point corresponding to each vibrating measurement is changed by an offset so that the integrated non-vibrating measurement matches the vibrating contact potential difference measurement at that point. This same offset is then applied to all data points in the corresponding track of the integrated, scaled non-vibrating data. For tracks that do not have a corresponding vibrating measurement, the appropriate offset is computed by interpolating or extrapolating the offsets calculated for the nearest tracks that contain vibrating measurements.

The interpolation or extrapolation is accomplished using polynomial fitting, splines, or some other appropriate and conventional mathematical technique. In an alternative embodiment, vibrating measurements are taken along multiple lines that are perpendicular to the direction of motion of the scanning probe. Offsets between the vibrating and non-vibrating measurements at each vibrating measurement point are computed. If more than one of the vibrating measurements corresponds to the same track in the non-vibrating data, then the offset for each point on the track that corresponds to a vibrating measurement is calculated, and then the offsets are combined statistically to calculate a single offset to be used for that entire track. For example, the offset of the track may be calculated as the mean or median of the individual point offsets. As before, the tracks that do not have a corresponding vibrating measurement are given an offset determined by interpolating or extrapolating the calculated offsets for nearby tracks. Both of these last two embodiments may also be used in the case where multiple vibrating measurements are taken at various locations on the wafer that are not necessarily arranged in lines.

In an alternative embodiment, a wafer is scanned with a non-vibrating contact potential difference sensor to produce tracks of data, and this first set of tracks is integrated and multiplied by an appropriate scaling factor to convert the integrated data into relative surface potential values. The scaling factor is determined using the method described above. The non-vibrating contact potential difference sensor is also used to acquire one or more tracks of data by moving the sensor perpendicular to the direction of motion during the first scanning operation. This second scanned track, or tracks, is also integrated and scaled to convert the integrated data into relative surface potential values. One or more vibrating contact potential difference measurements are then made on each of the second set of tracks. Offsets are calculated between the vibrating contact potential difference measurements and the corresponding points on the second set of tracks, and the resulting offsets are then applied to all points in each of the second set of tracks. As a result of this operation, the second set of tracks represents the actual contact potential difference values along each track. The difference is then calculated between the values on this second set of tracks and the corresponding points on the first set of tracks. These differences are used to calculate an offset for each track in the first set of tracks. The calculated offset for each track in the first set is applied to all points in that track. In this case, vibrating contact potential difference measurements are used to transform the second set of track data into absolute contact potential difference values. These absolute contact potential difference values are then used to calculate offsets for the first set of tracks. In this method, a large number of tracks in the first set is calibrated using contact potential difference values calculated for a smaller number of tracks in the second set. The second set of tracks is acquired by moving the non-vibrating sensor in a direction that is perpendicular to the direction of scanning used to acquire the first set of tracks. The second set of tracks is calibrated using one or more vibrating contact potential difference measurements. In one embodiment, the second set of tracks consists of a single track that is calibrated using a single vibrating contact potential difference measurement.

In another preferred embodiment, the non-vibrating contact potential difference sensor is scanned radially to form concentric tracks of data. Each track is integrated and multiplied by an appropriate scaling factor to convert to relative contact potential difference values along each track. Discrete-point vibrating measurements are then made along a radius of the wafer. The difference between each vibrating measurement and the corresponding integrated, scaled non-vibrating data point is calculated and applied to the entire circular track containing that point. Offsets for tracks that do not correspond to vibrating measurements are calculated by interpolating or extrapolating the offsets of the two or more closest tracks which correspond to vibrating measurements. This method calculates a unique offset for each track. The offset provides information on the variation in contact potential difference in the radial direction as determined by the vibrating contact potential difference measurements. If there is charging or other surface effects that vary with radius, the computed offset will be different for different tracks. For example, dielectric charging caused by a single wafer clean or plasma processing operation often exhibits a radial surface potential pattern. This type of charging will result in different offsets for different track radii, and can be detected and measured in the resulting integrated, scaled and transformed image.

In another preferred embodiment, the wafer surface is scanned radially with a non-vibrating contact potential difference sensor and the resulting data is integrated and scaled to convert it to relative surface potential values. Vibrating contact potential difference sensor measurements are then made at several different locations on the wafer surface, where multiple measurements may be taken at the same radius. If multiple vibrating contact potential difference measurements are made on the same track, the offset for that track is calculated from the multiple offsets using a statistic such as the mean or median. As before, once a single offset value has been computed for each radial track corresponding to a vibrating contact potential difference measurement, the resulting offset values are interpolated or extrapolated to calculate offsets for tracks that do not contain vibrating measurements. The image that results from applying offsets to each track of the integrated, scaled non-vibrating contact potential difference sensor image represents the contact potential difference at each point on the scanned surface and includes information on radial variations in surface potential or contact potential difference.

These and other objects, advantages, and features of the invention, together with the organization and manner of operation thereof, will become apparent from the following detailed description when taken in conjunction with the accompanying drawings, wherein like elements have like numerals throughout the several drawings described below.

DETAILED DESCRIPTION OF THE PREFERRED EMBODIMENTS

Figure 1:
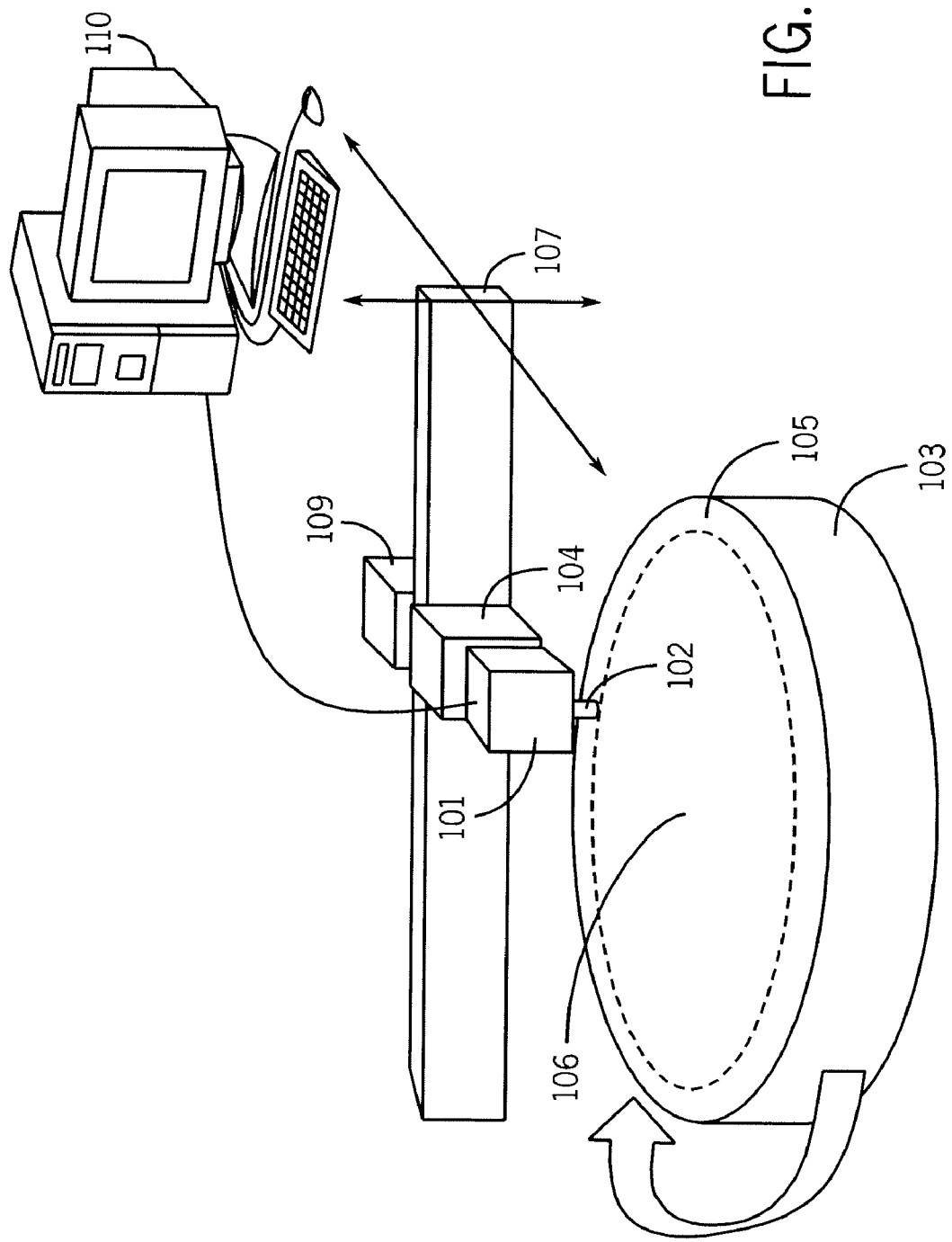
FIG. 1 shows a diagram of a wafer inspection system with a system for fixturing and rotating a wafer, a system for positioning a sensor above a wafer, a contact potential difference sensor, a system for vibrating the contact potential difference sensor perpendicular to the wafer surface, and a component for processing data from the sensor.

In accordance with one preferred embodiment, a radial scanning apparatus 100 is shown in FIG. 1. The apparatus 100 consists of a contact potential difference sensor 101, a system 103 for mechanically fixturing wafer 105 and spinning the wafer 105 to generate relative motion between probe tip 102 and wafer surface 106 such that the probe tip 102 moves parallel to the wafer surface 106, a system 107 for positioning the sensor 101 a fixed distance above the wafer surface 106, a system 104 for vibrating the probe tip perpendicular to the wafer surface, and a system 110 for acquiring and processing the output signal from the sensor 101 to identify and classify wafer 105 non-uniformities. In this preferred embodiment, the contact potential difference sensor 101 can be operated as a non-vibrating contact potential difference sensor to scan the wafer surface 106 and generate data on changes in contact potential difference across the wafer surface 106, or as a vibrating contact potential difference sensor to generate measurements of the absolute contact potential difference between the sensor probe tip 102 and one or more points on the wafer surface 106. In an alternative embodiment, two or more different sensors can be used for non-vibrating and vibrating measurements.

In one preferred embodiment, the semiconductor wafer 105 is placed on the conductive wafer fixture 103. This may be done manually or using an automated process such as, but not limited to, a wafer handling robot. The wafer 105 is held in place, such as by using vacuum. Alternative methods of holding the wafer 105 include, but are not limited to, electrostatic forces and edge gripping. In one embodiment, the fixture 103 is mounted to a spindle which can rotate the wafer 105 about its center. The non-vibrating contact potential difference sensor 101 is attached to a positioning system 107 that can adjust the height of the sensor 101 above the wafer surface 106 and can move the sensor 101 radially from at least the center of the wafer 105 to one edge of the wafer 105. The contact potential difference sensor 101 is electrically connected to the wafer surface 106 via the conductive wafer fixture 103. In one embodiment, a height sensor 109 that has been calibrated to the height of the contact potential difference sensor probe tip 102 is also mounted on the same positioning system 107 as the contact potential difference sensor 101.

A system 104 for vibrating the contact potential difference sensor 101 perpendicular to the wafer surface 106 is attached to the contact potential difference sensor 101. This system 104 is used to make vibrating Kelvin probe measurements of the contact potential difference between the probe tip 102 and the wafer surface 106.

After the wafer 105 is secured to the fixture 103, the height sensor 111 is positioned above one or more points on the wafer surface 106 and the height of the wafer surface 106 is measured when deemed appropriate. These wafer height measurements are used to calculate the position of the contact potential difference sensor 101 that will produce the desired distance between the probe tip 102 and the wafer surface 106. This information is used to position the probe tip 102 at a fixed height above the wafer surface. The probe tip 102 is then moved to the desired height at a point above the outside edge of the wafer 105 using the positioning system 107.

As shown for example in FIG. 1, the probe 101 is held stationary and the wafer 105 is rotated on the wafer fixture 103 such that the probe tip 102 moves relative to the wafer 105 along a circular path that is centered at the wafer 105 center. Data is acquired during a single rotation of the wafer 105. In this case the probe 101 is operating in a non-vibrating contact potential difference sensing mode, and generates data that is representative of changes in contact potential difference across the surface of the wafer 105. The sensor 101 is then moved a programmable distance along the radius of the wafer 105 towards the wafer center. Another rotation of data is acquired at this new radius. The probe tip 102 continues to step and scan concentric circular regions of the wafer 105 until the probe reaches the center of the wafer 105. The resulting data is then assembled into an image of the wafer 105 as shown, for example, in FIG. 3. Alternately, each concentric circular region of the wafer 105 could be scanned multiple times and the resulting data averaged to reduce the effect of random noise. In one embodiment, this image is processed to identify and classify non-uniformities, this processing can take many forms.

The differential sensor data is integrated to generate an image which represents regions with different surface potential values. Integration is performed by calculating the sequential sum of values in each track of the differential data. The integrated track data is then multiplied by a scaling factor to convert the integrated data to approximate relative contact potential values. This scaling factor is calculated for a particular scanning method by performing a least-squares linear fit between multiple vibrating Kelvin probe measurements and the integrated non-vibrating contact potential difference data values at the same points on a wafer surface. Once the scaling factor has been calculated for a particular scanning sensor and method, it can be applied to integrated non-vibrating contact potential difference data acquired on subsequent wafers to convert the data to relative surface potential values. Additional methods exist for calculating and applying the scaling factor. For example, the scaling factor can be calculated once using a test or calibration wafer and then applied to all subsequent wafers, or the scaling factor can be calculated during the inspection of each wafer using the integrated non-vibrating contact potential difference data and some set of vibrating Kelvin probe measurements on the surface of the wafer.

Figure 4A:
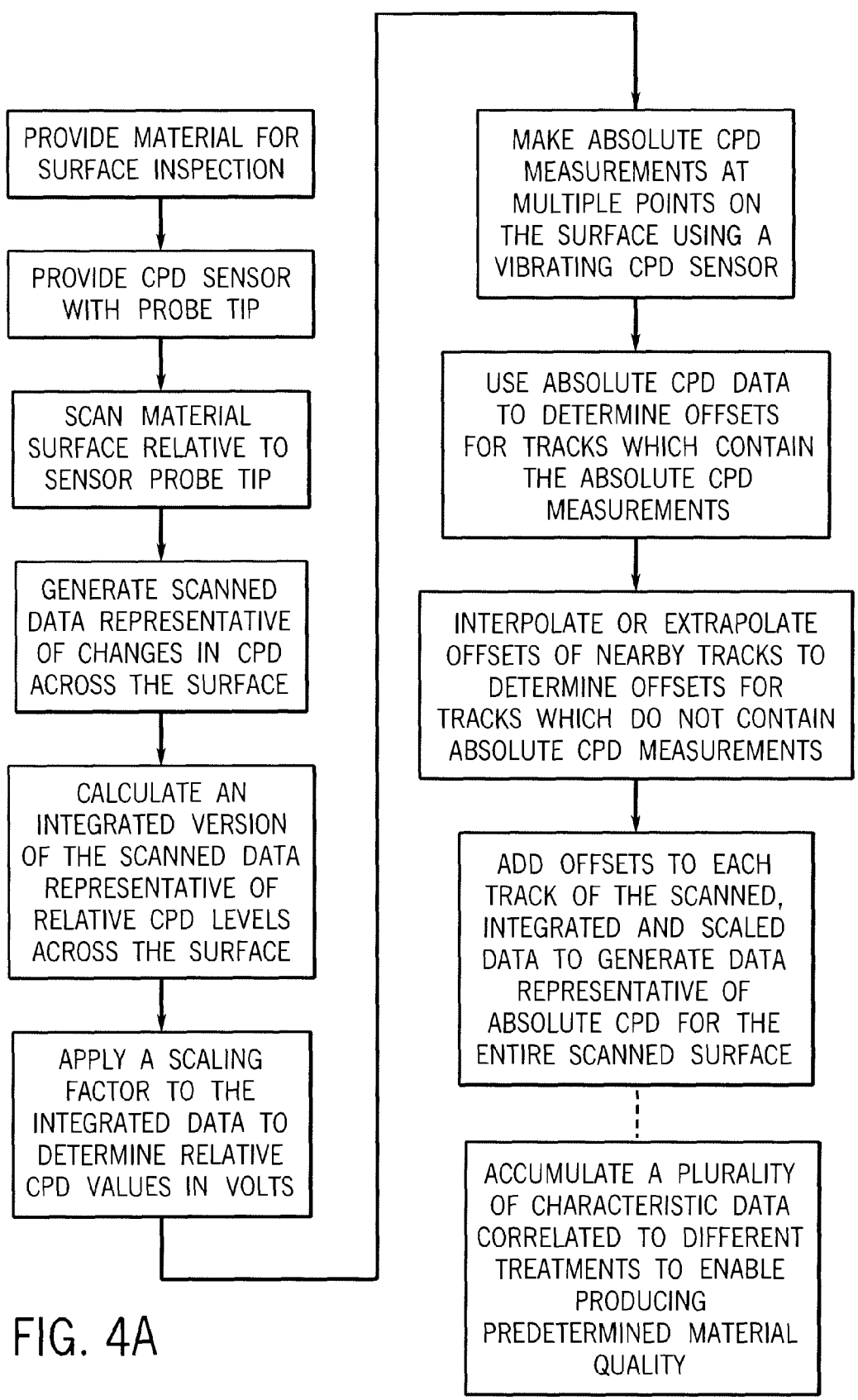
FIG. 4A shows a functional block flow diagram of a generic method of the invention.
Figure 4B:
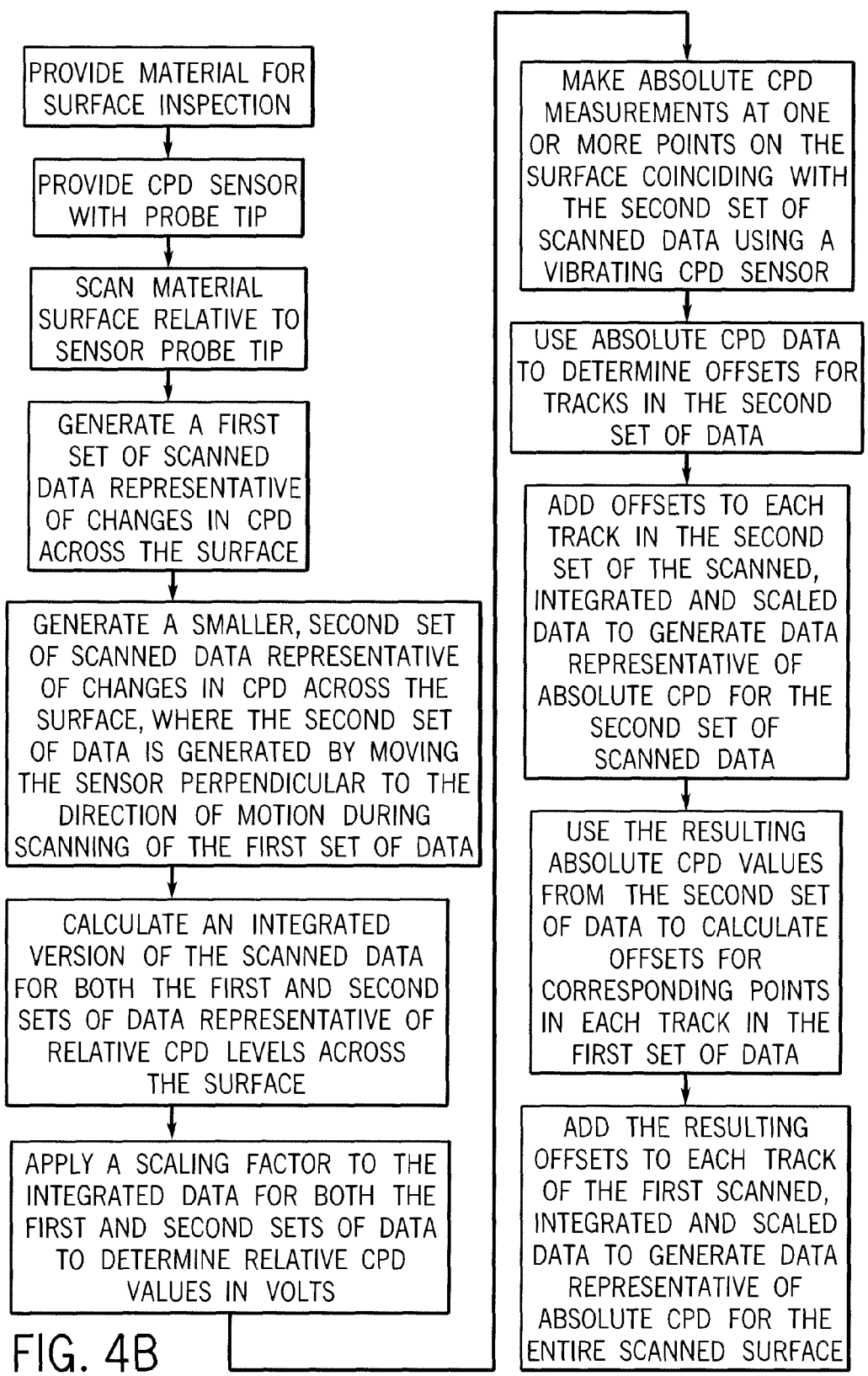
FIG. 4B shows an alternative method of the invention.
Figure 4C:
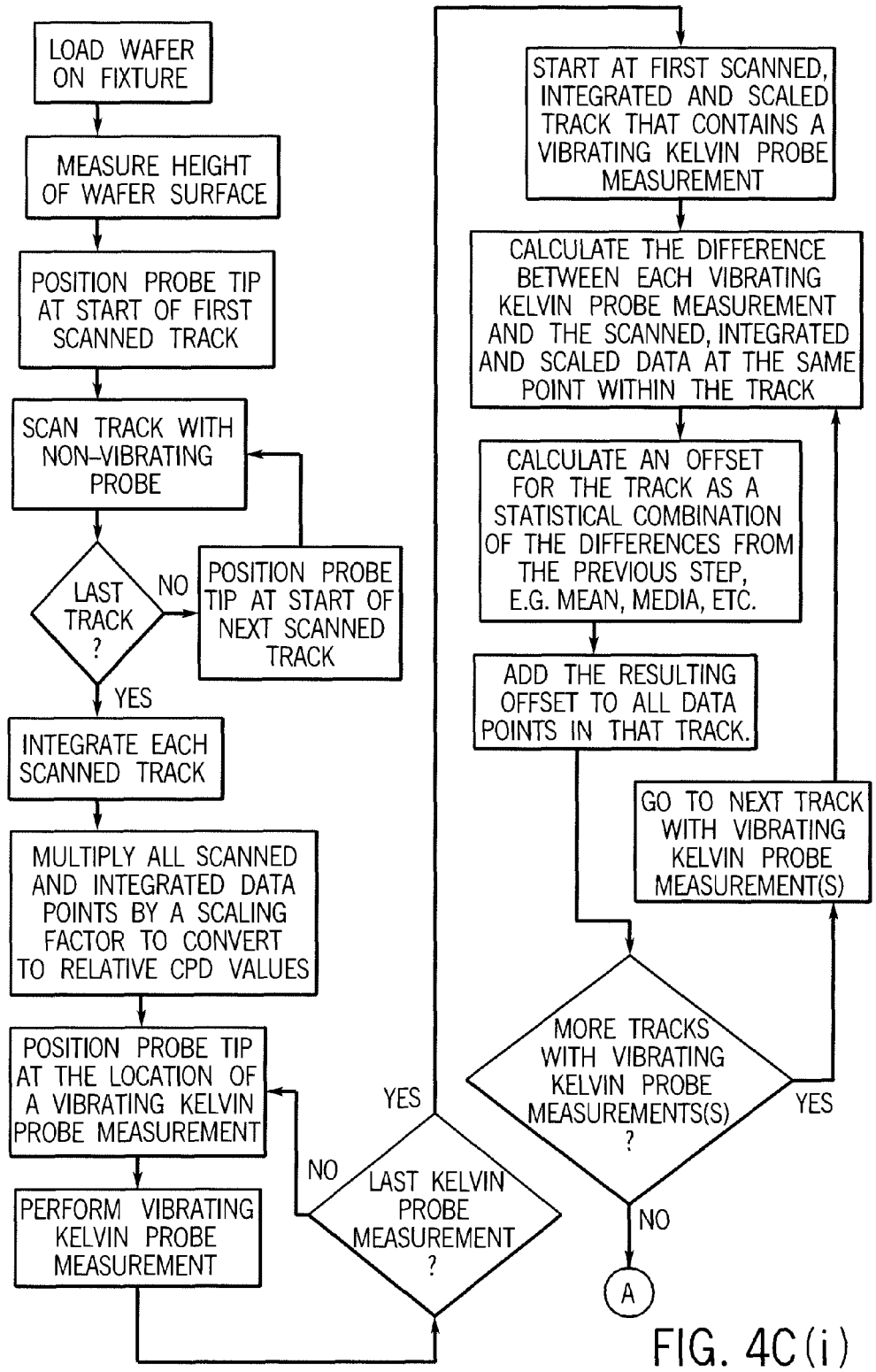
FIG. 4C(i) and FIG. 4C(ii) show a preferred embodiment for a method of the invention.

In a preferred embodiment illustrated by the flow charts of FIGS. 4A-4C, multiple vibrating Kelvin probe measurements are taken at different radii from the wafer center. For each vibrating Kelvin probe measurement, the difference between the vibrating Kelvin probe value and the value of the integrated scaled non-vibrating contact potential difference data at the same point is calculated. This difference, or offset, is then added to each point in that particular circular track of the integrated scaled data. If more than one vibrating Kelvin probe point lies on the same track, the offset for that track is calculated as the mean or median of all of the offsets for all of the vibrating Kelvin probe measurements that lie on that particular track. If a track does not contain any vibrating Kelvin probe measurements, the offset for that track is calculated by interpolating the offset values for the two or more closest tracks on either side of the track. If the track does not lie between two tracks with vibrating Kelvin probe measurements, the offset for that track is calculated by extrapolating the offsets for the two or more closest tracks with vibrating Kelvin probe measurements. Using this method, an offset is calculated and applied to each circular track of integrated scaled data. The resulting image represents contact potential difference values for the entire scanned surface. This image includes radial variations in contact potential difference, because offsets calculated from vibrating Kelvin probe measurements at different radii result in track offsets that represent these radial differences.

Figure 2:
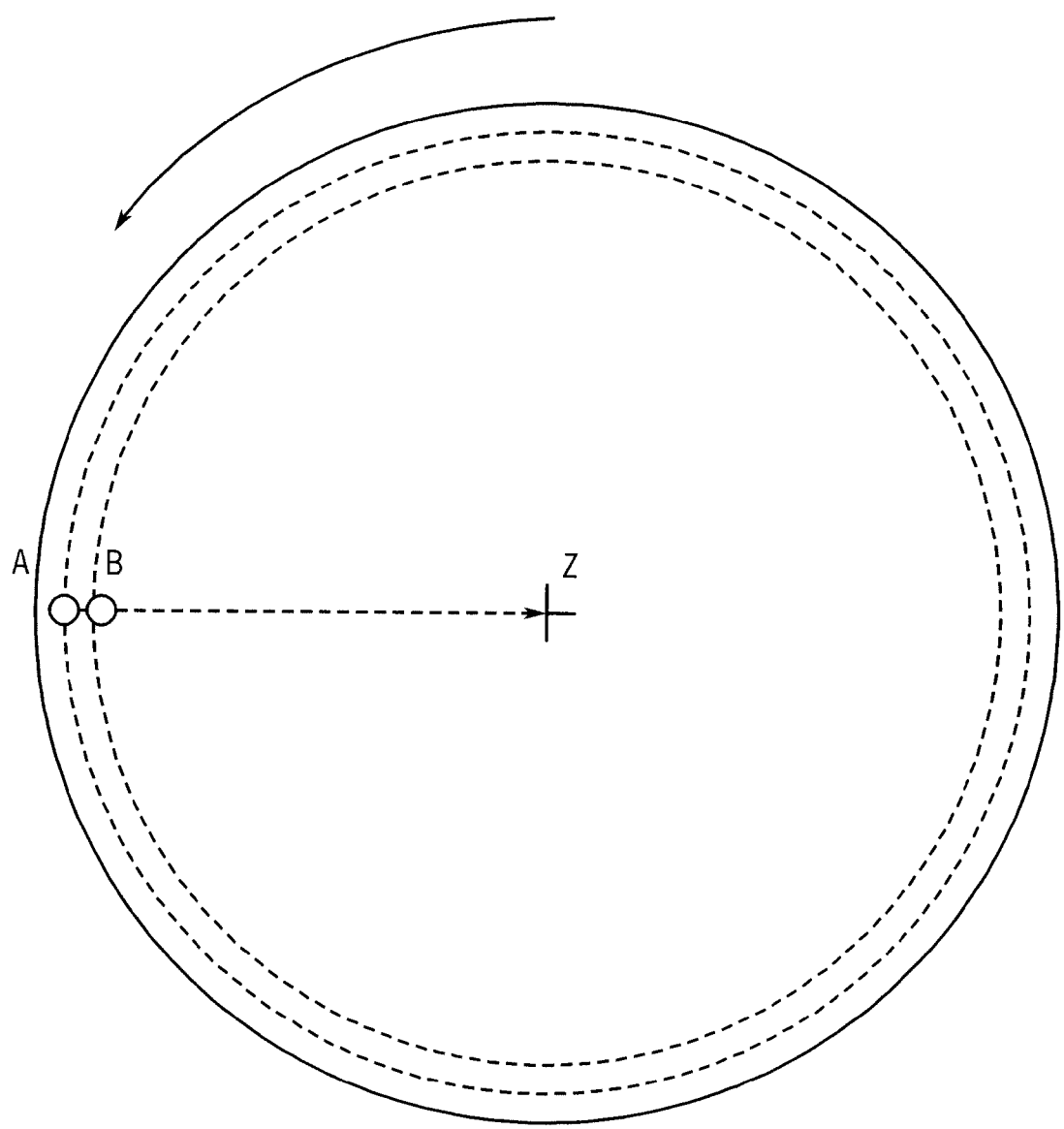
FIG. 2 shows operation of a radial scanning system.
Figure 3:
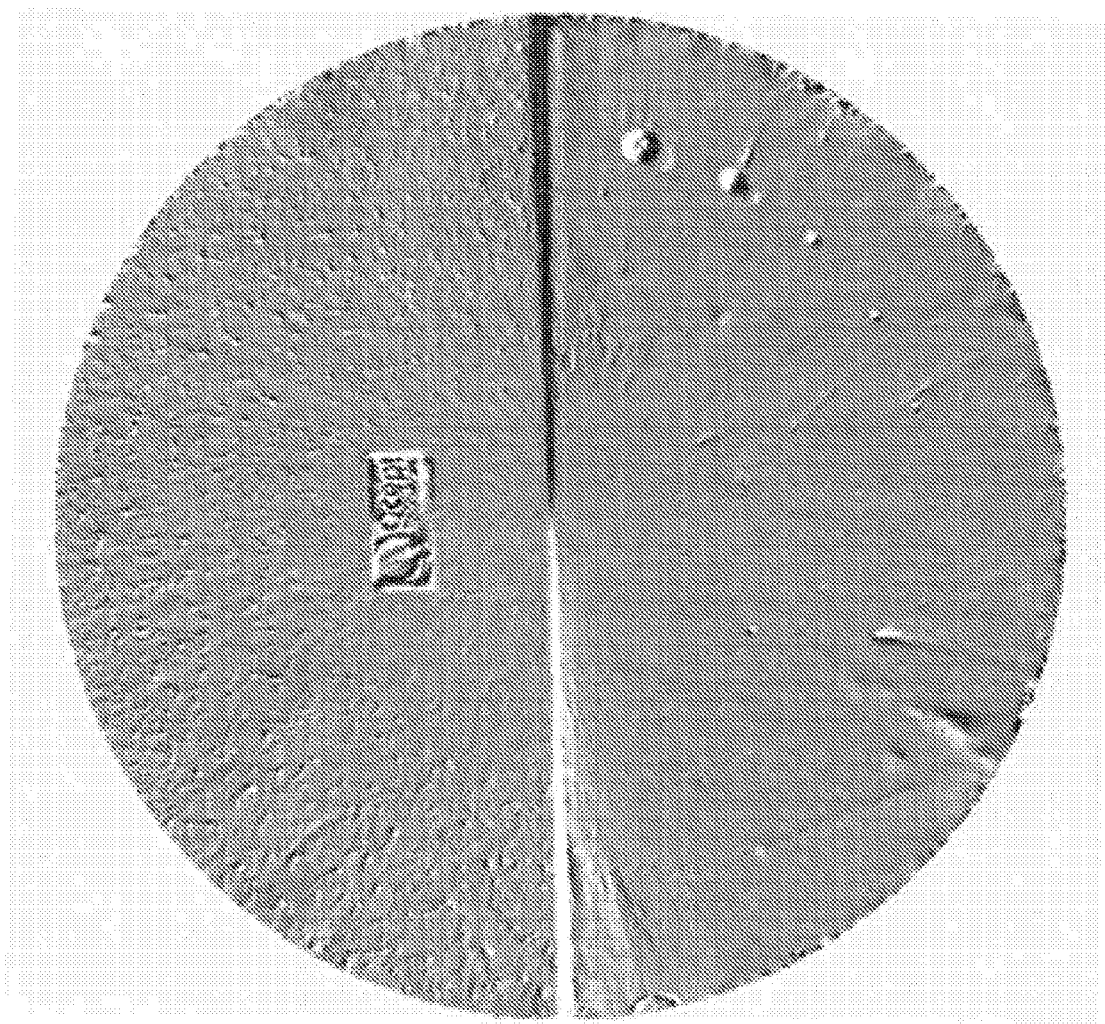
FIG. 3 shows a sample image created by radially scanning a wafer as in FIG. 2 with a non-vibrating contact potential difference sensor.

FIG. 2 shows a diagram of the radial scanning method of one preferred embodiment of the present invention. The contact potential difference sensor probe tip 102 is positioned at point "A" near the edge of the wafer 105. The wafer 105 is rotated on the wafer fixture 103 and a circular track of data is scanned. The probe tip 102 is moved a programmable distance towards the wafer 105 center to point "B" and a second circular track of data is scanned. This process is repeated until the probe tip 102 reaches the center of the wafer 105. The resulting data is combined into an image representing changes in contact potential difference across the wafer surface 106. In this case, the sensor is operated as a non-vibrating contact potential difference sensor. A sample wafer image acquired using this scanning method is shown in FIG. 3 (this and the other samples are off the shelf, commercial grade silicon single crystal wafers). The light and dark regions represent increases and decreases in contact potential difference due to material changes on the surface of the wafer.

Figure 5:
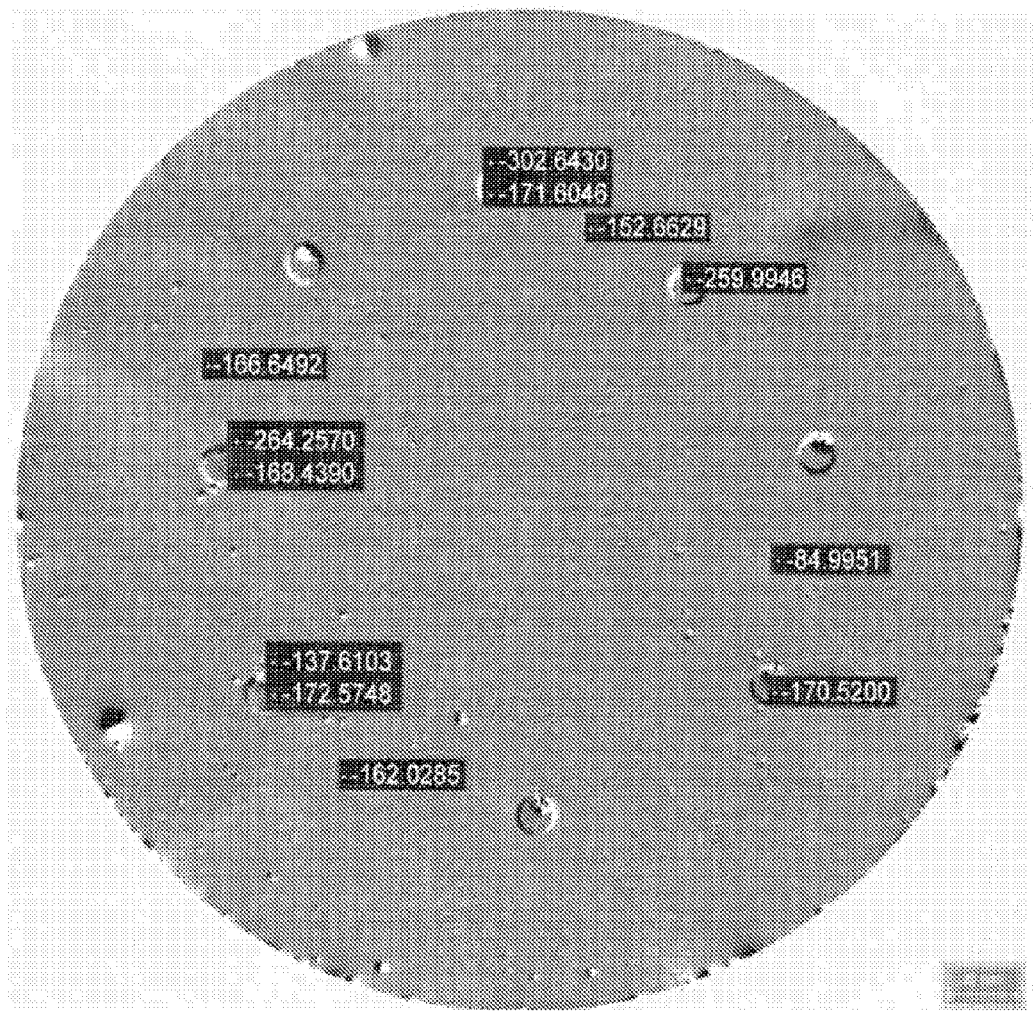
FIG. 5 shows an image created by radially scanning a wafer with a non-vibrating contact potential difference sensor and then performing vibrating Kelvin probe measurements at selected identified locations on the image.
Figure 6:
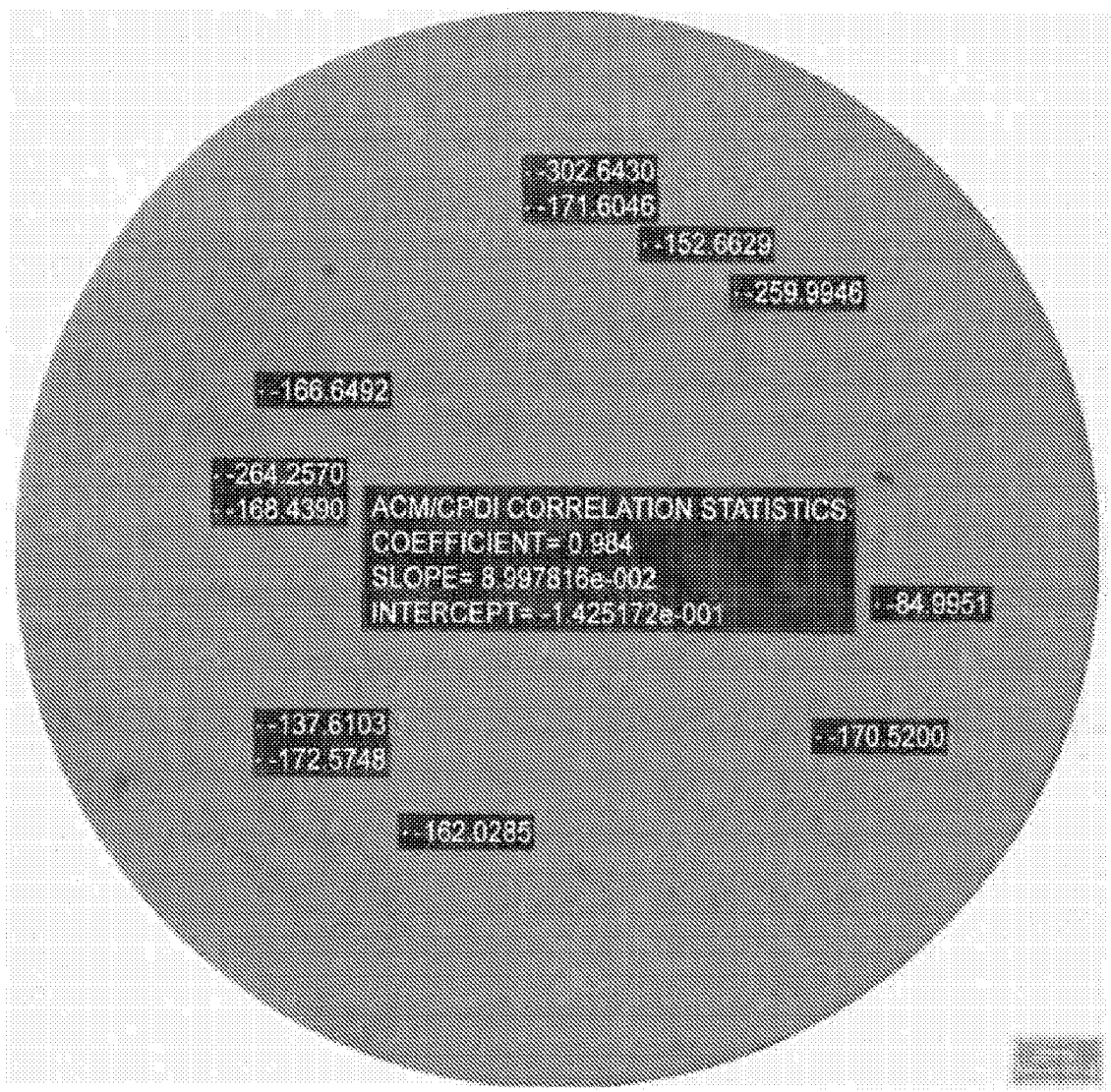
FIG. 6 shows an image of the same wafer image shown in FIG. 5 after integration and calculation of a least-squared error line fit to the vibrating Kelvin probe measurements such that the image shows the slope and offset values calculated for the linear transformation that converts integrated scanned values to absolute contact potential difference values.

The differential non-vibrating contact potential difference sensor signal can be integrated and scaled to form a signal that represents relative surface potential. FIGS. 5 and 6 show the process of calculating an appropriate scaling factor for converting integrated scanned data into relative surface potential values. FIG. 5 shows the differential data generated by scanning a wafer with a non-vibrating contact potential difference sensor. FIG. 5 also shows the locations and values of vibrating contact potential difference measurements. These vibrating contact potential difference measurements are in millivolts. FIG. 6 shows the image which results from integrating the image in FIG. 5. This image shows regions of relative surface potential. FIG. 6 also shows the results of calculating a least squares fit between the vibrating contact potential difference values and the integrated non-vibrating contact potential difference data at the same points. A scale factor is calculated which can be applied to subsequent images. This scale factor is shown as a slope of 8.997816e-2, or approximately 0.09. The correlation coefficient of the integrated non-vibrating contact potential difference measurements and vibrating contact potential difference measurements is also shown on the image. In this case, the correlation coefficient is 0.984, indicating a good fit between the two sets of data.

Figure 7:
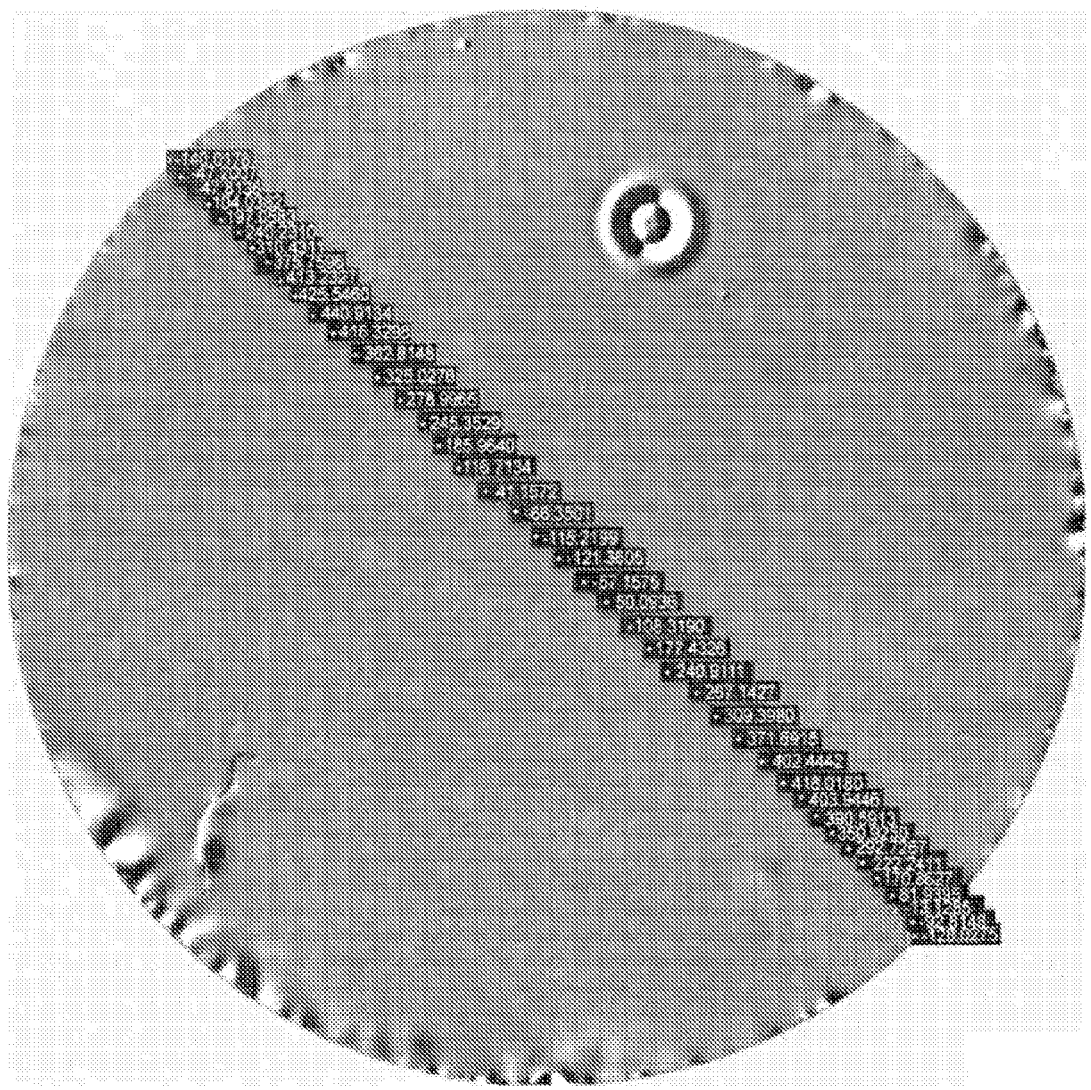
FIG. 7 shows a non-vibrating contact potential difference scanned image of a first wafer with vibrating Kelvin probe measurements identified at data points along a diameter of the wafer.
Figure 8:
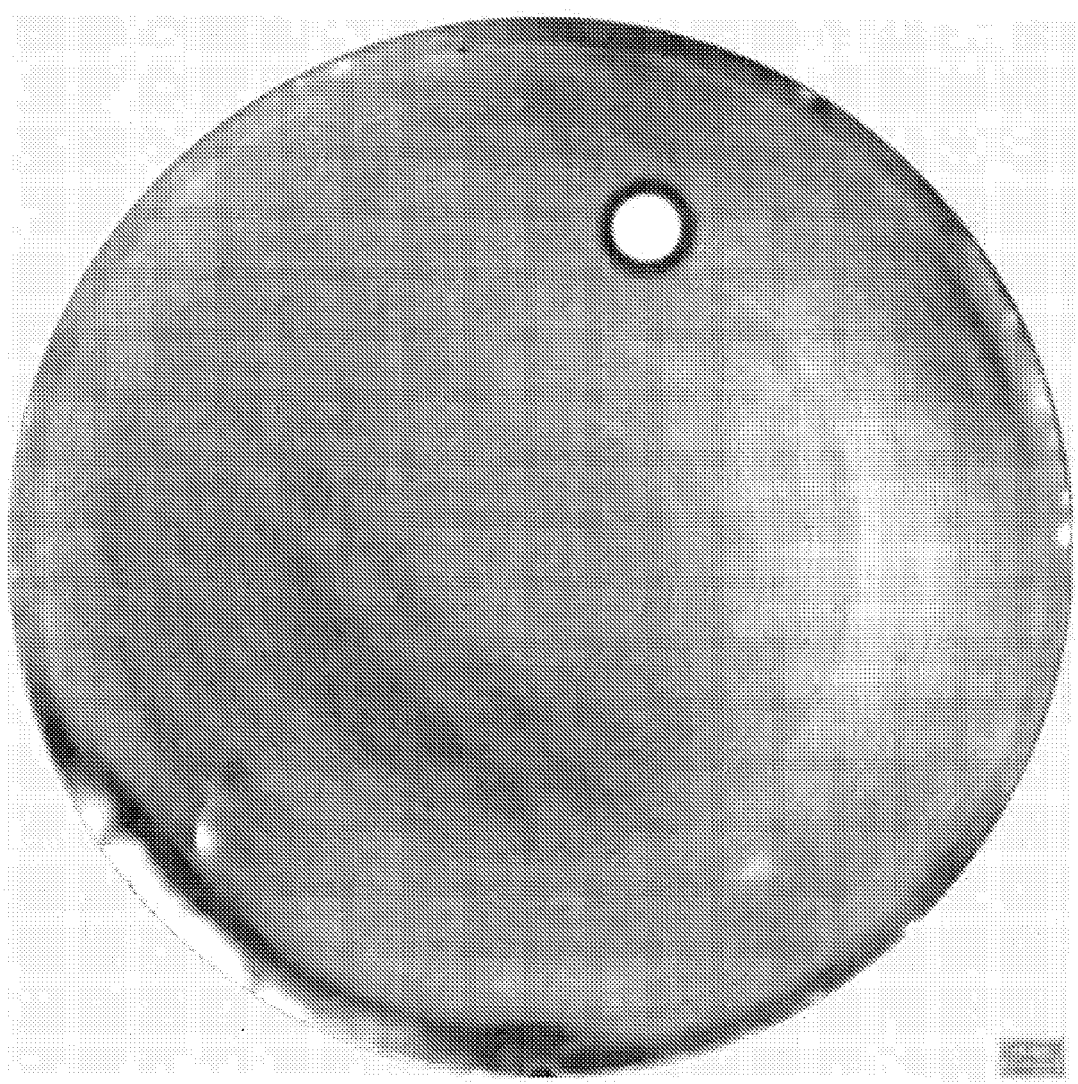
FIG. 8 shows the image from FIG. 7 after integration and scaling (no vibrating probe measurements included), and minimal radial variation of surface potential or work function is visible in this image.
Figure 9:
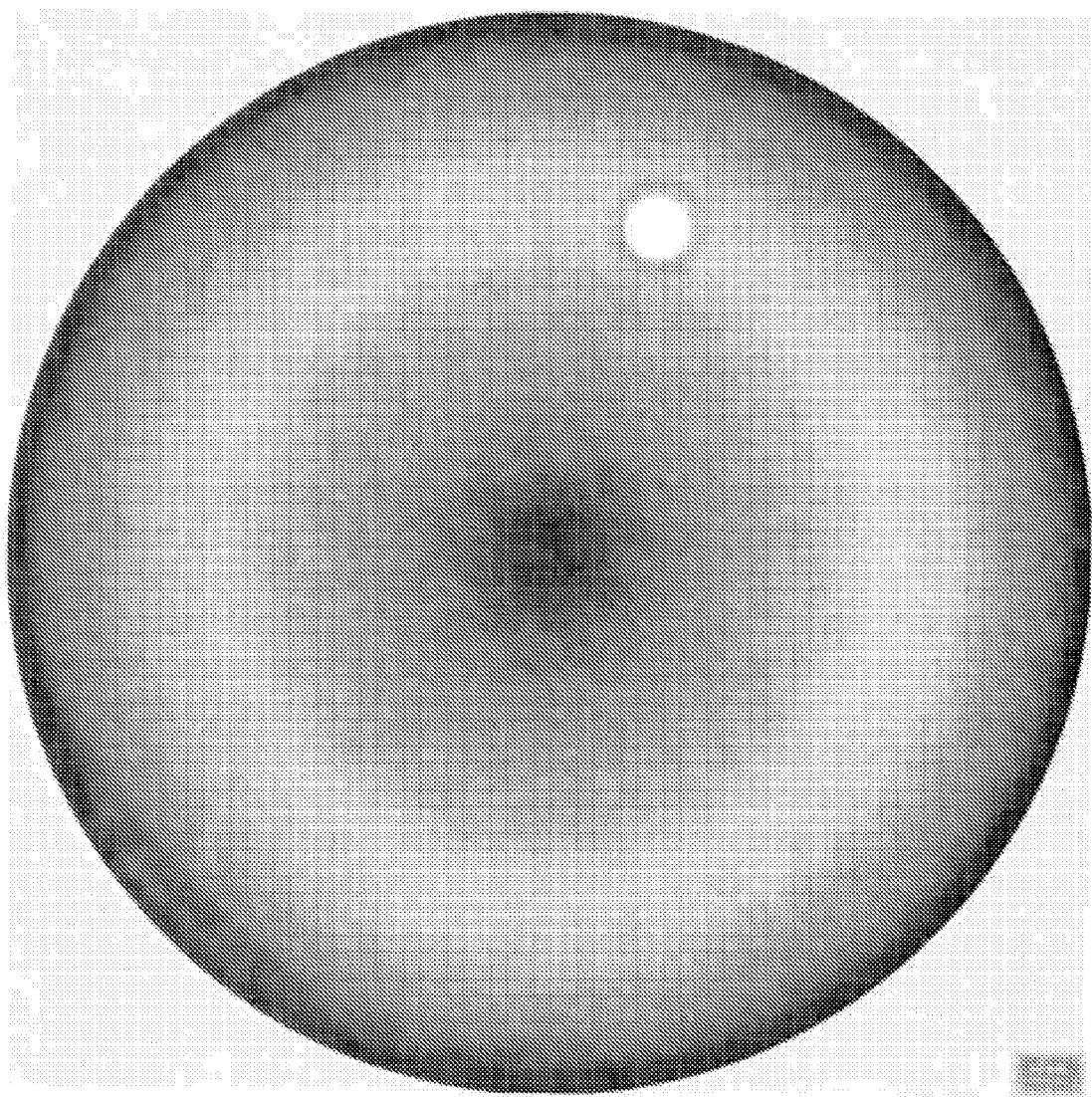
FIG. 9 shows the image from FIG. 7 after offsetting each track based on the vibrating Kelvin probe measurements such that an offset is calculated and applied to each track based on the vibrating Kelvin probe measurement made on the track or on nearby tracks.

FIG. 7 shows the differential non-vibrating contact potential difference image of a first wafer 105 along with the locations and results of radial vibrating contact potential difference measurements. The wafer samples of FIGS. 7-19 were initially prepared by forming a thick thermal oxide coating of about 1000 Angstroms on the surface. The wafer was then cleaned and rinsed with deionized water applied to the center of the wafer while it was rotated. This particular wafer was processed using a first conventional system tool and a first type of deionized water conductivity, and with a given spin speed and ramp up/down rate. FIG. 8 shows the image in FIG. 7 after integration and scaling. FIG. 8 shows data which is representative of relative contact potential difference values, but does not include any information on radial variations in contact potential difference. FIG. 9 shows the same wafer image as FIG. 8 after individual track offsets have been calculated and applied to the integrated and scaled non-vibrating contact potential difference data so that the image data approximately matches the vibrating contact potential difference data at the same points. Once these steps have been completed, measurements can be performed at any radius of the wafer 105 to determine reliable contact potential difference values which can be plotted and/or analyzed. These integrated, scaled and offset data show significant radial variation in contact potential difference that is not evident in the differential or integrated images shown in FIGS. 7 and 8.

Figure 10:
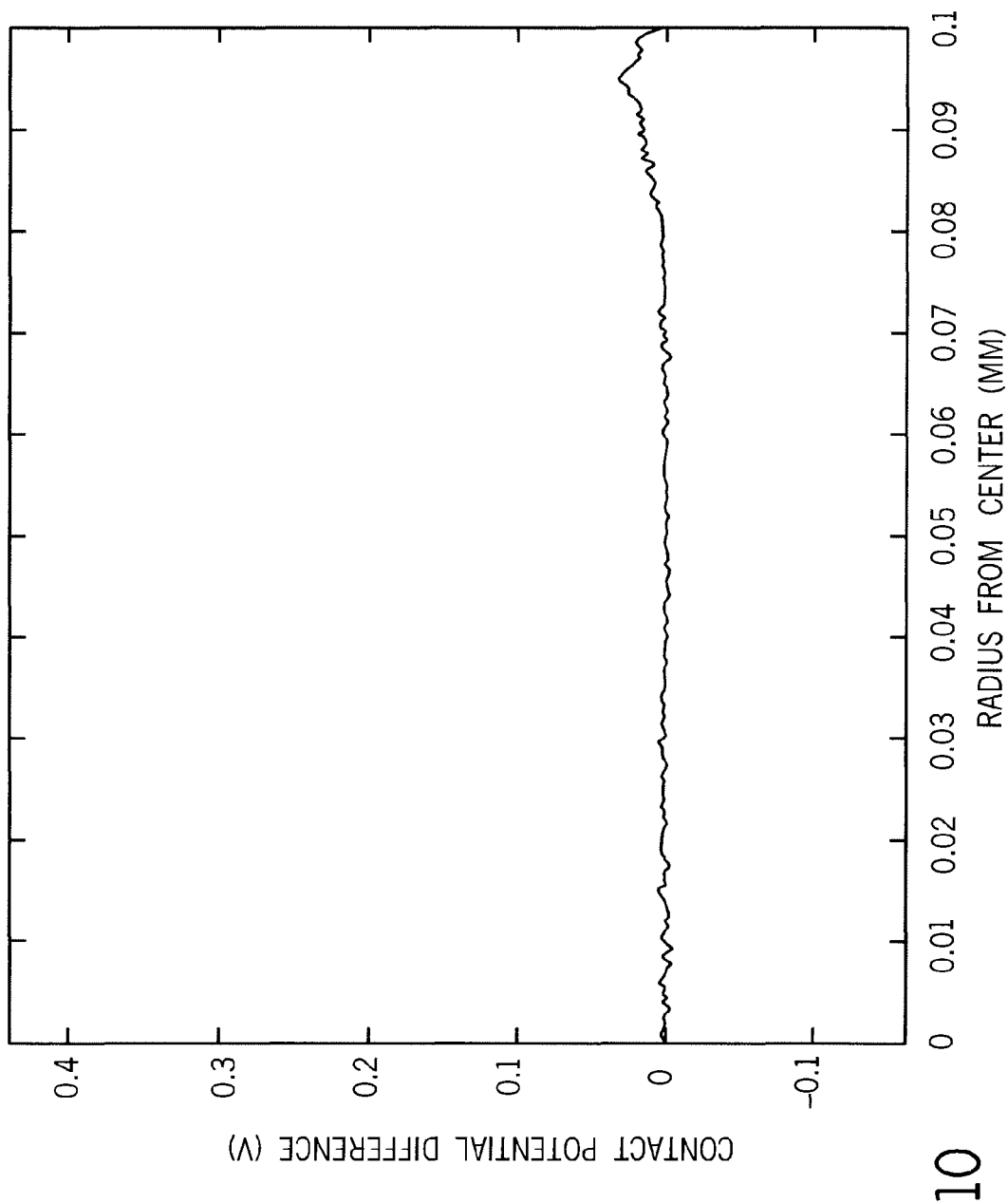
FIG. 10 shows a linear plot taken from the image values taken along one radius for the wafer image data of FIG. 8.
Figure 11:
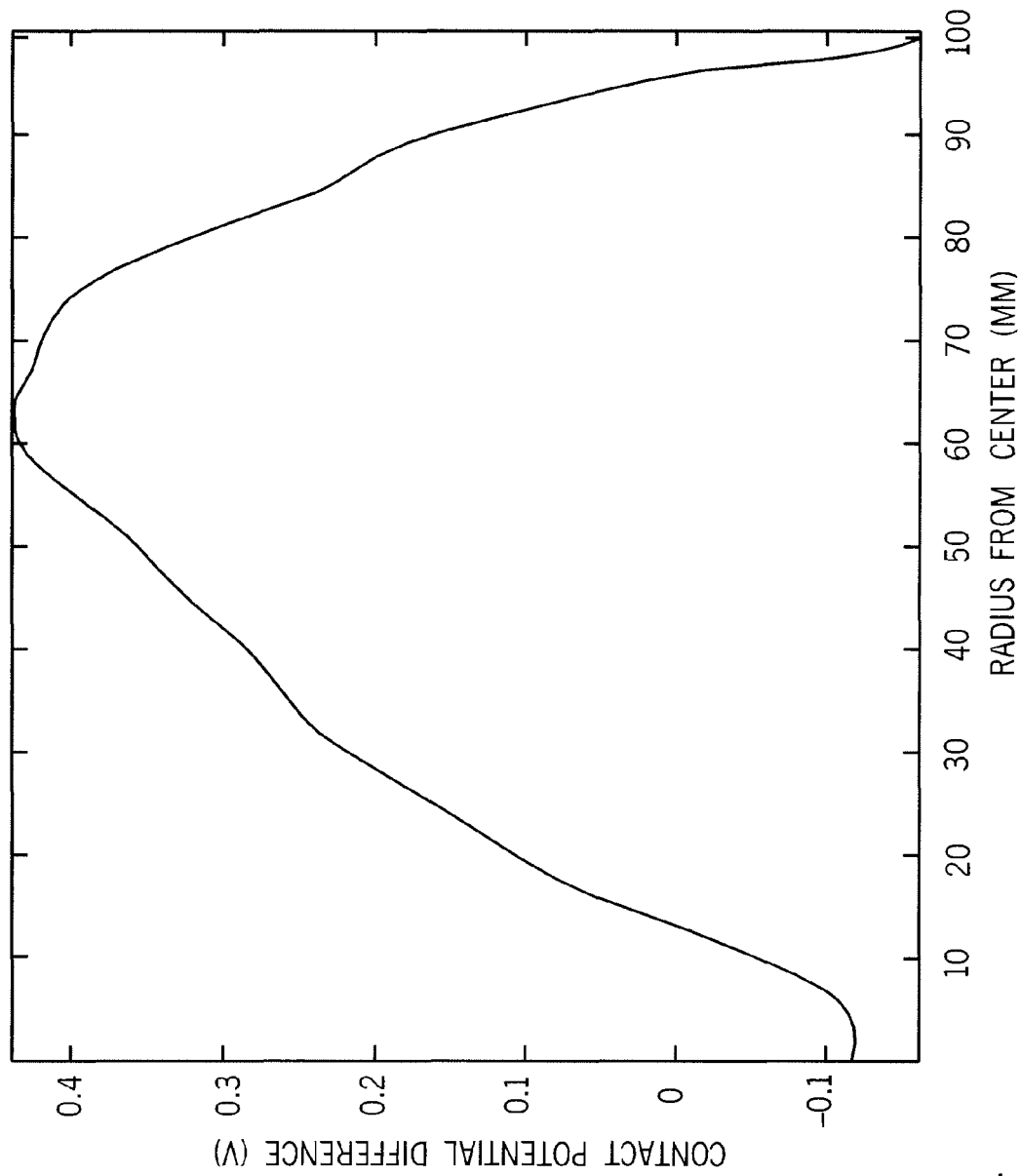
FIG. 11 shows a linear plot taken from the image values along a radius in the wafer image data shown in FIG. 9.

FIG. 10 shows a plot of image values along one radius of the image shown in FIG. 8. No significant radial variation is evident in this plot. FIG. 11 shows a plot of image values along the same radius of the image shown in FIG. 9. In this case, substantial radial variation is evident in the signal. The use of this invention provides a wafer image that represents the contact potential difference between the probe tip and the wafer surface at all points, and includes information on the radial variation in contact potential difference that is not available from the non-vibrating data alone.

Figure 12:
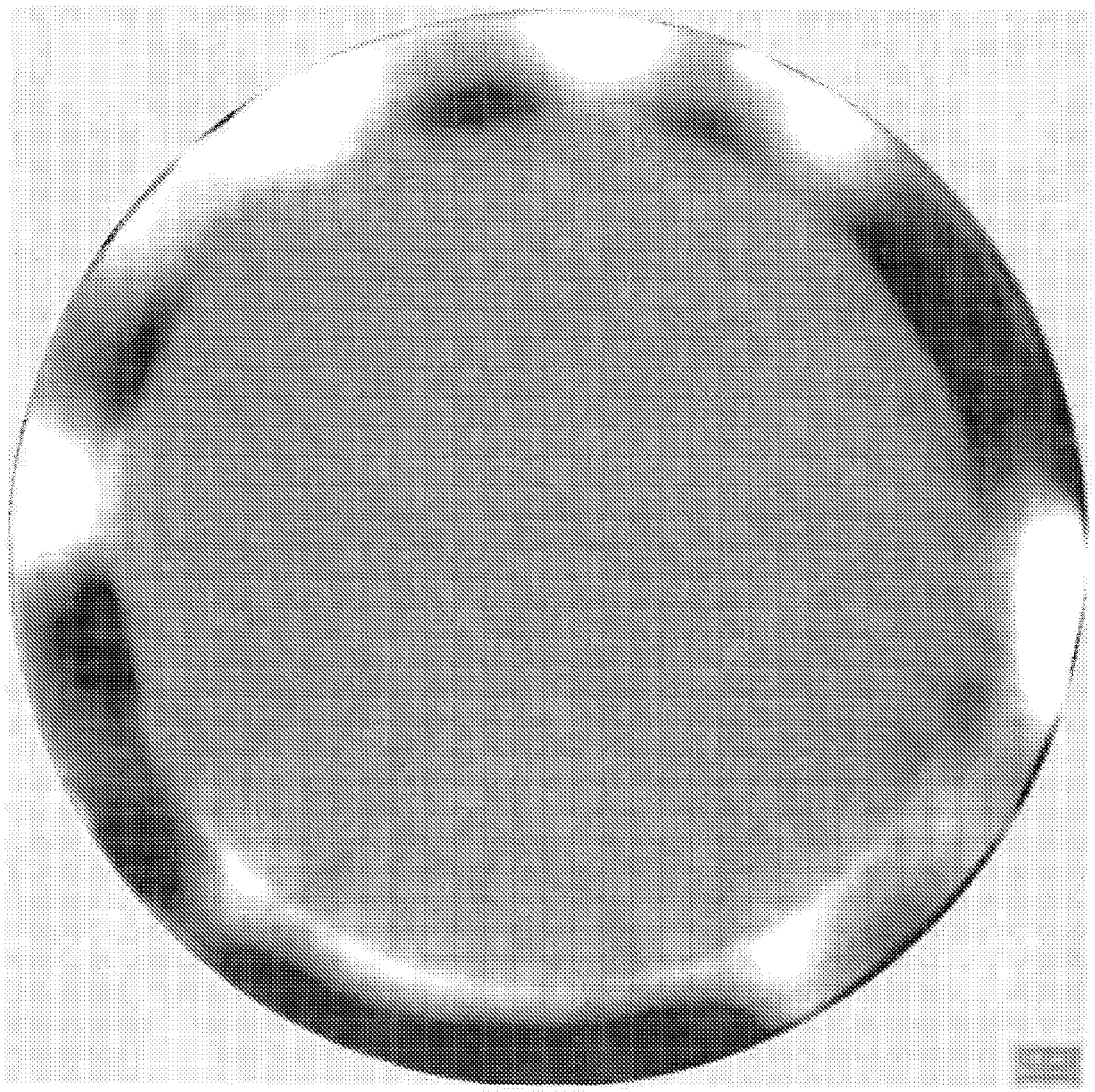
FIG. 12 shows a non-vibrating contact potential difference scanned image of a second wafer (no vibrating probe measurements) after integration and scaling, and minimal radial variation of surface potential or work function is visible in the image.
Figure 13:
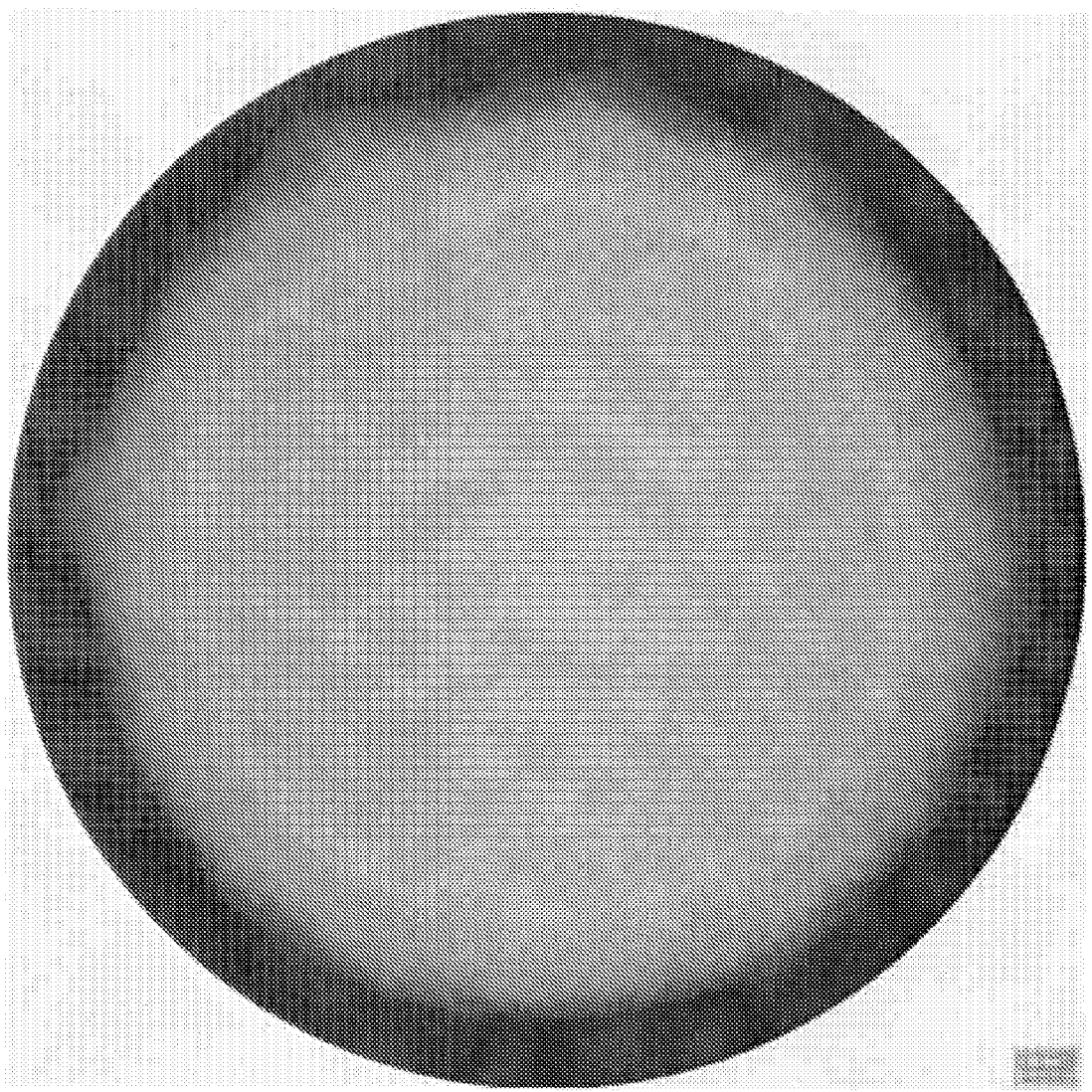
FIG. 13 shows the image from FIG. 12 after offsetting each track based on the vibrating Kelvin probe measurements such that an offset is calculated and applied to each track based on vibrating Kelvin probe measurement made on the track or on nearby tracks.

FIG. 12 is another example of an integrated image of a second wafer 105 which has undergone a radial scan using a non-vibrating contact potential difference probe. This wafer underwent a same generic treatment as the wafer of FIG. 7 except the conventional tool used was a different one and under different water conditions (mainly different conductivity) and tool spin conditions. FIG. 13 shows the sample image from the wafer of FIG. 12 after the integration and scaling operation and using vibrating probe measurements as described hereinbefore. Again, detailed measurements and analysis can now be performed as was done for the first wafer 105 to determine contact potential difference values along any radius of the second wafer 105.

Figure 14:
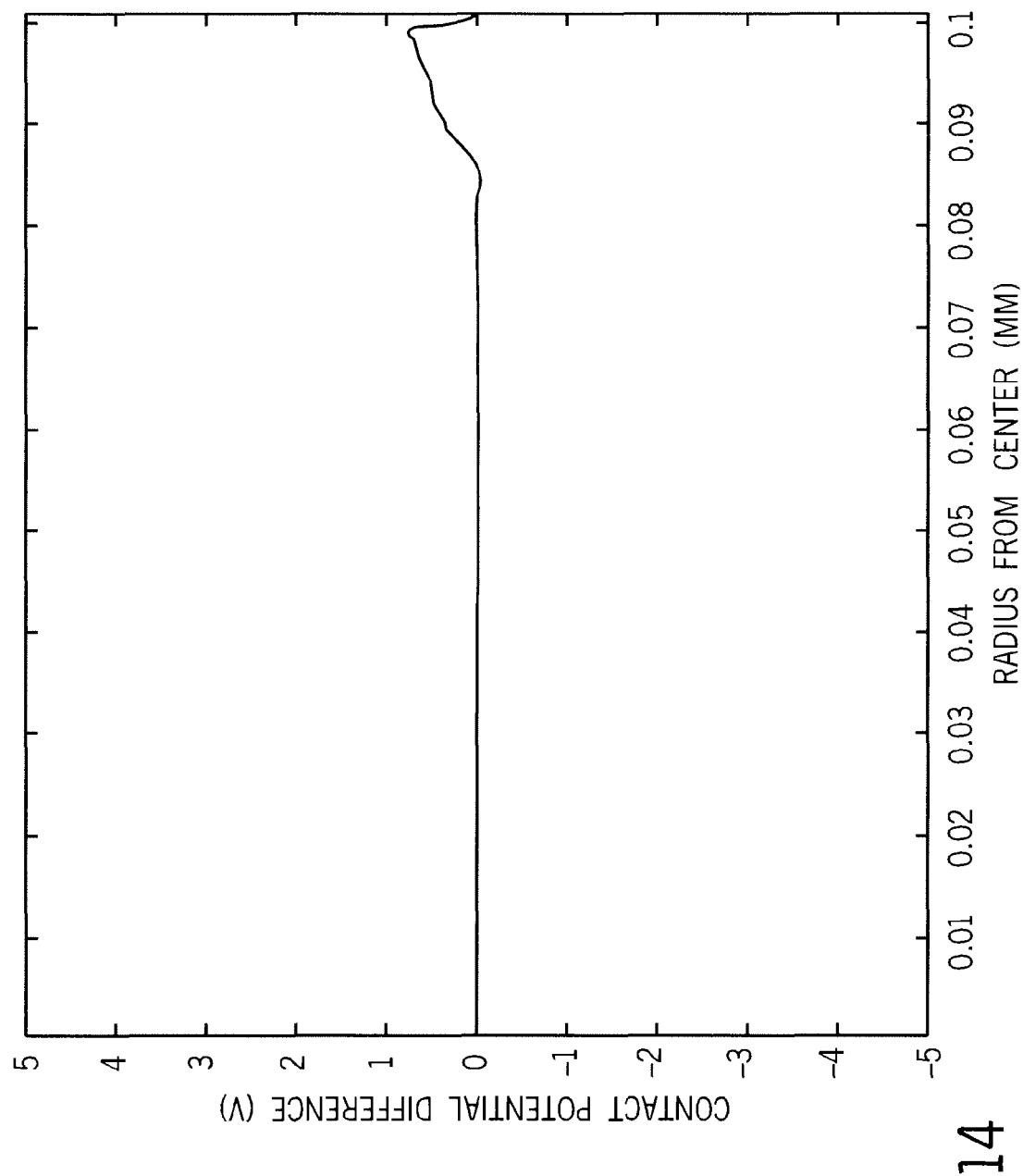
FIG. 14 shows a linear plot of image values taken along a radius of FIG. 12.
Figure 15:
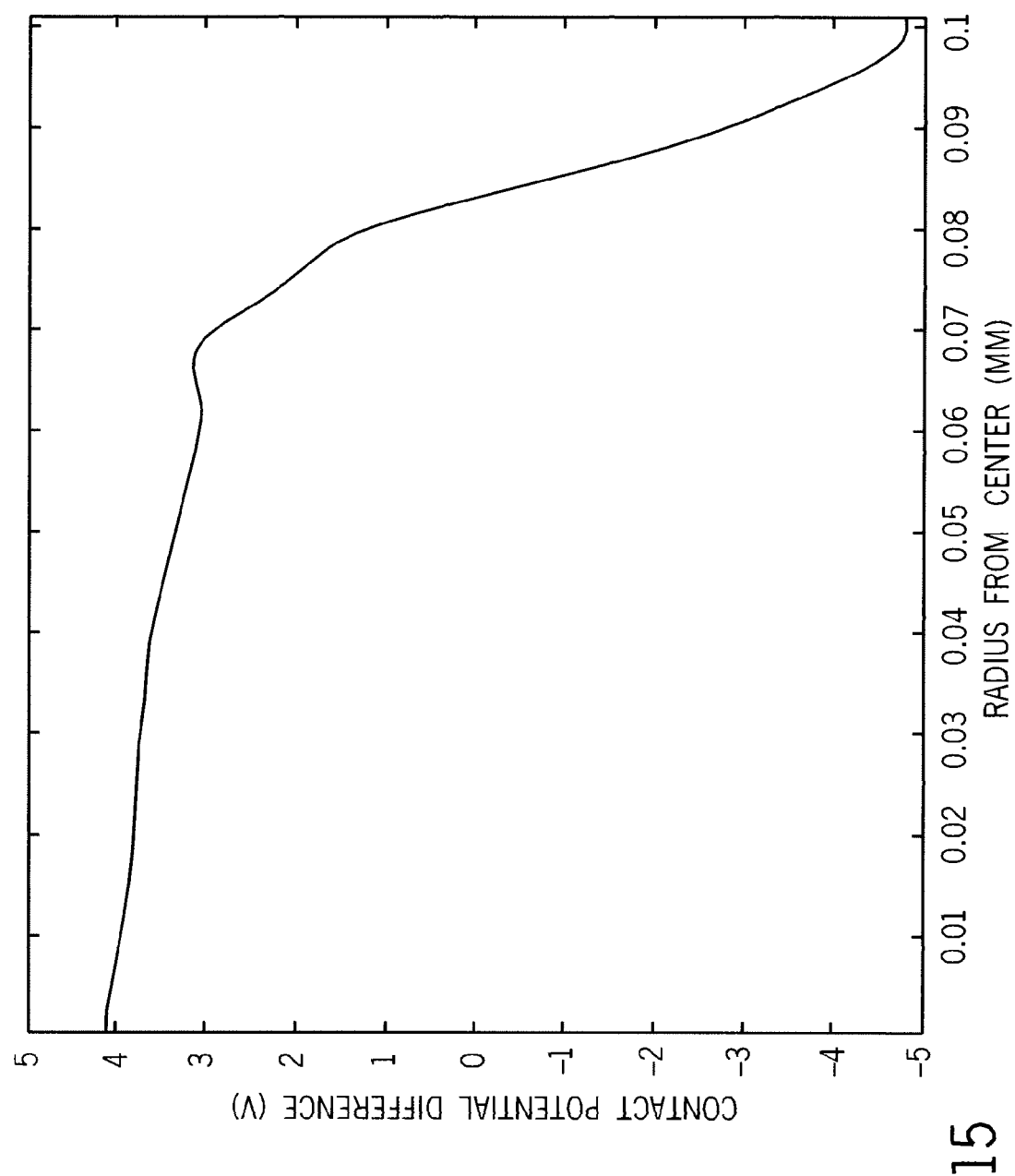
FIG. 15 shows a linear plot of image values taken along a radius for the image of FIG. 13.

FIG. 14 shows a linear plot of image values along an exemplary radius of FIG. 12 showing minimal radial variation. A small amount of radial variation is evident near the edge of the wafer, but this is an artifact of the integration process and the large signal values near the edge of the wafer; and do not accurately represent the radial variation in surface potential. FIG. 15 shows a like linear plot as for FIG. 14 but for image values along a radius of FIG. 13 and showing the substantial and correct radial variations.

Figure 16:
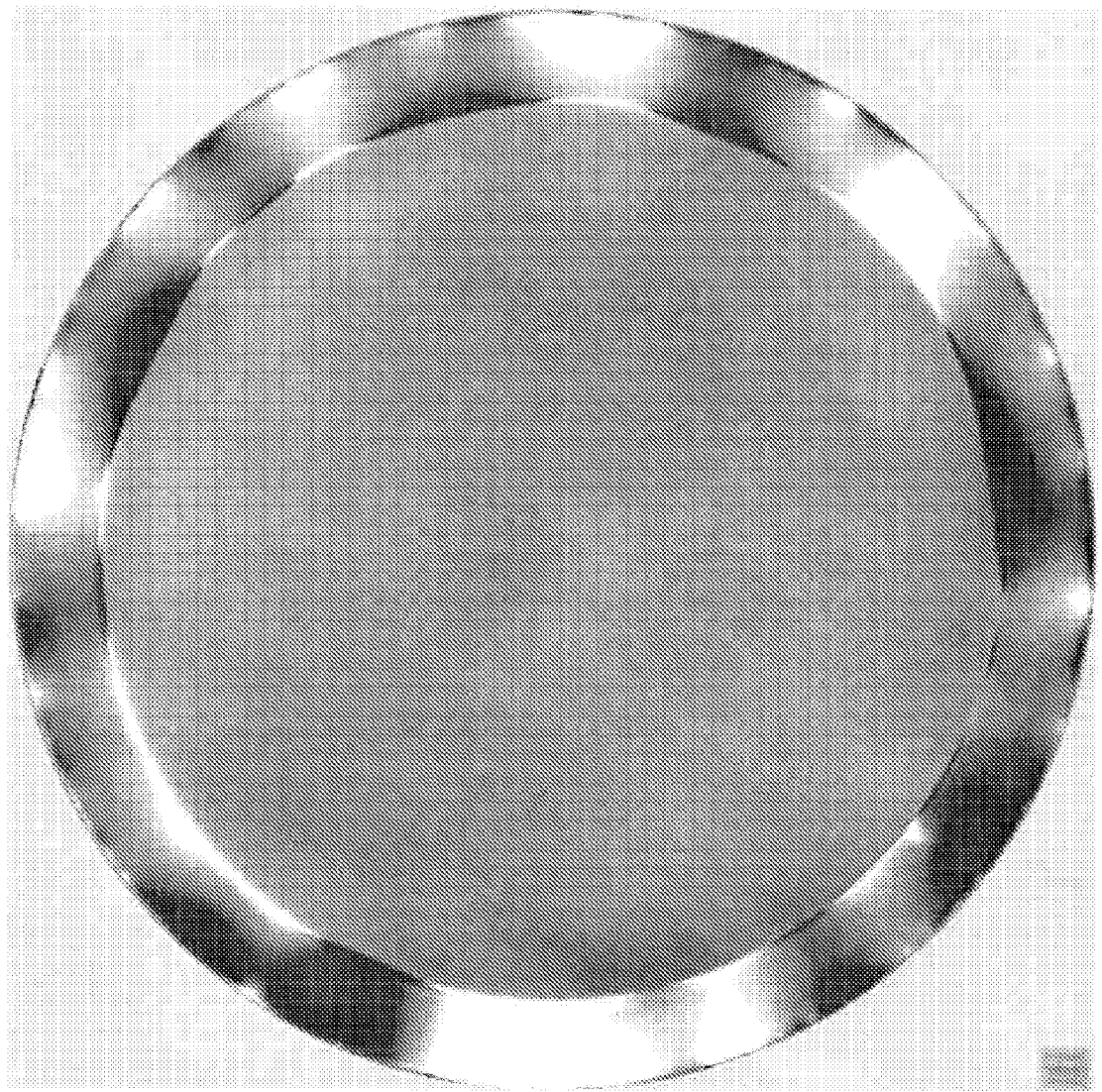
FIG. 16 shows a non-vibrating contact potential difference scanned image of a third wafer (no vibrating probe measurements) after integration and scaling and minimal radial variation of surface potential or work function is visible in the image.
Figure 17:
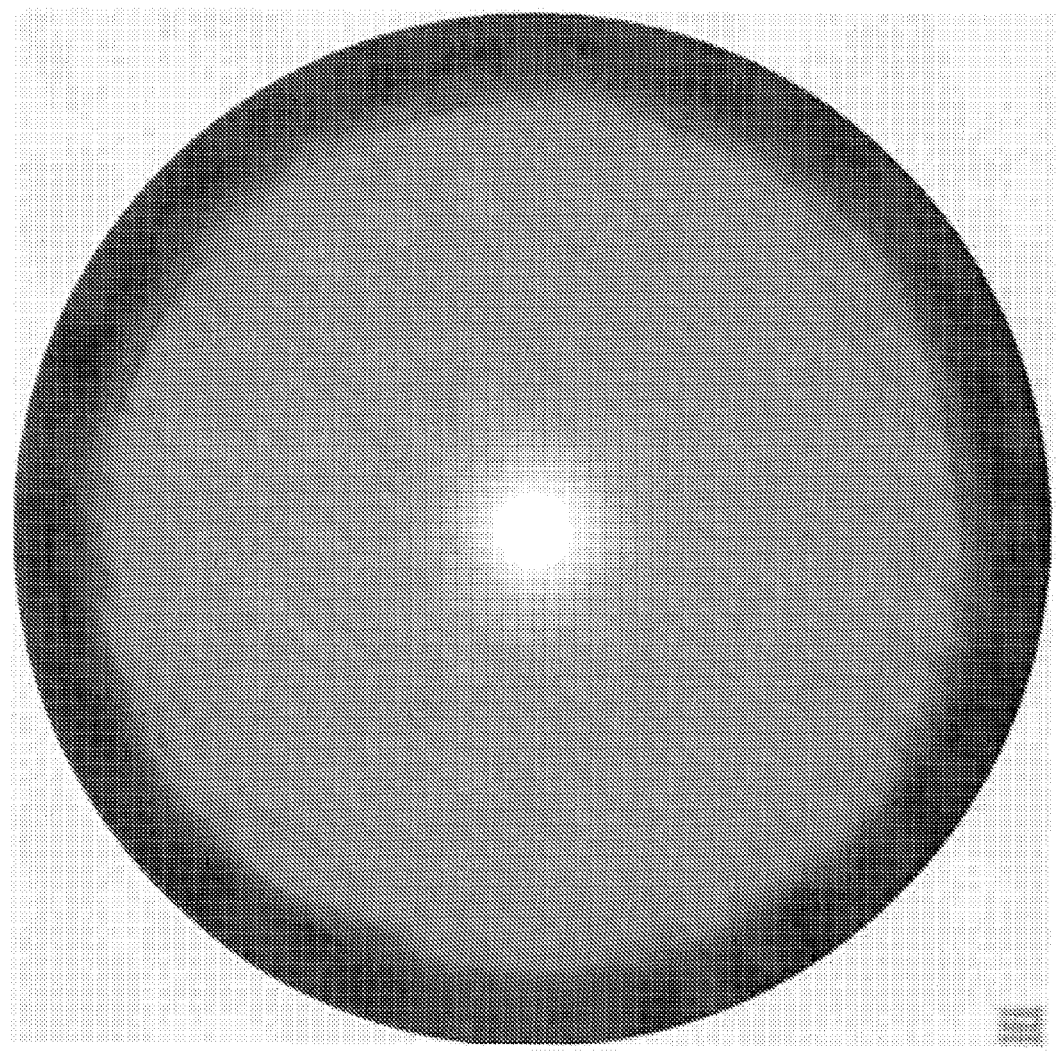
FIG. 17 shows the sample image from FIG. 16 after offsetting each track based on the vibrating Kelvin probe measurements such that an offset is calculated and applied to each track based on the vibrating Kelvin probe measurement made on the track or on nearby tracks.

FIG. 16 is a third example of an integrated image of a third wafer 105 which has undergone a radial scan using a non-vibrating contact potential difference probe. Once again, a different standard tool, different water conditions and different spin conditions were used to treat the wafer. FIG. 17 shows the sample image from the wafer of FIG. 16 after the integration and scaling operation and using vibrating probe measurements as described hereinbefore.

Figure 18:
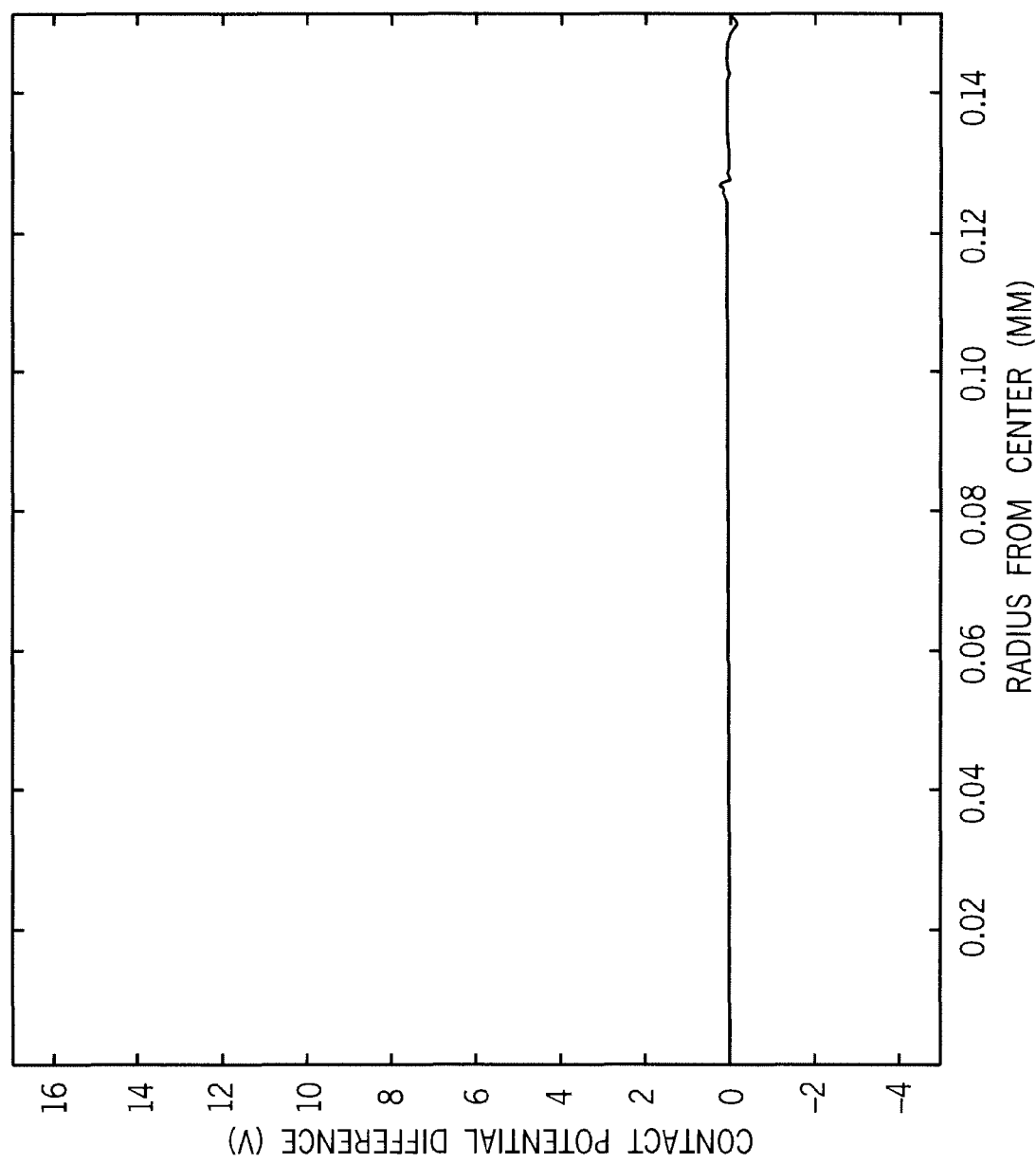
FIG. 18 shows a linear plot of image values taken along a radius of the image data of FIG. 16.
Figure 19:
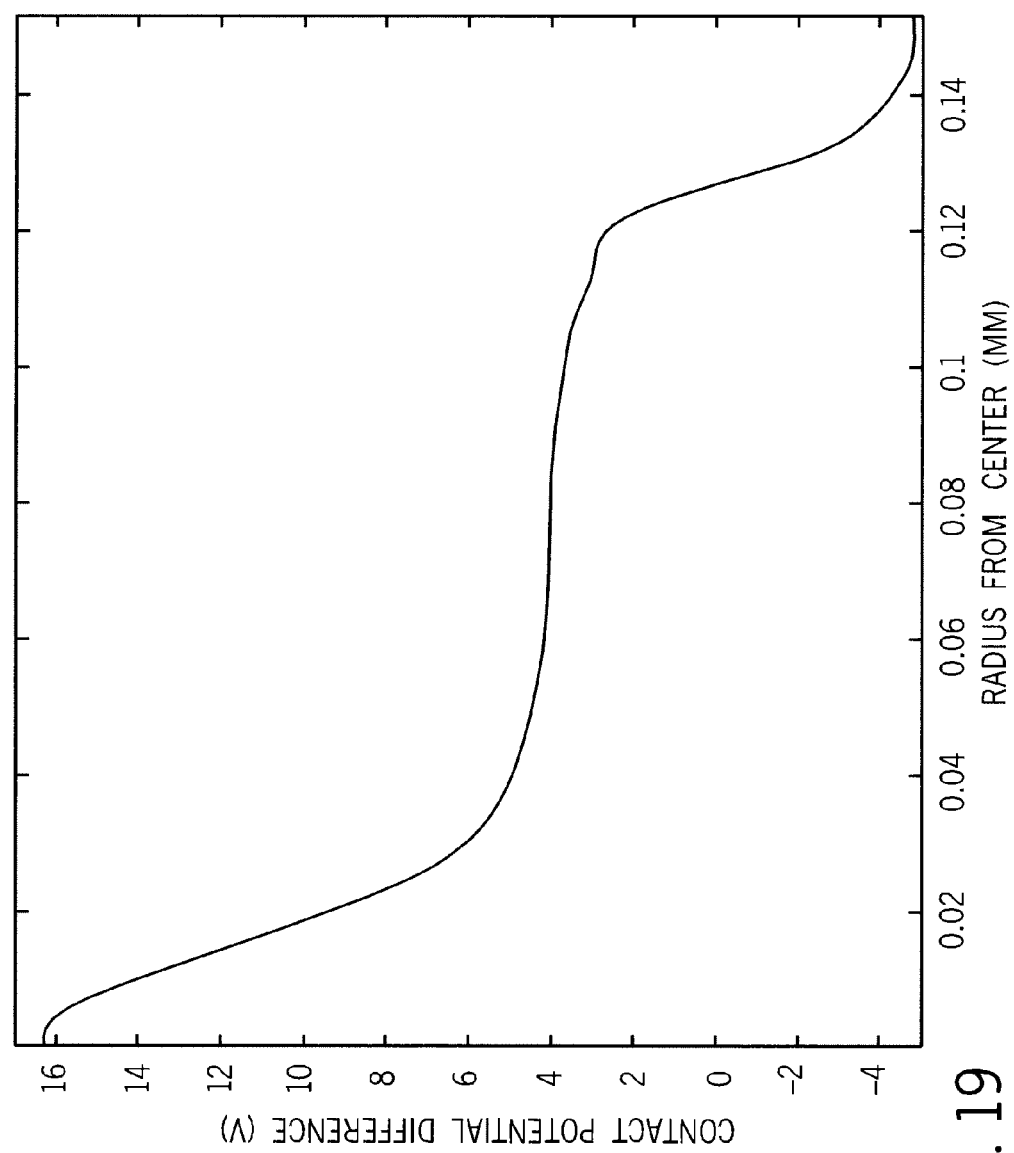
FIG. 19 shows a linear plot of image values taken along a radius of FIG. 17 showing significant radial variation.

FIG. 18 shows a linear plot of image values along an exemplary radius of FIG. 16 showing minimal radial variations except the different edge portion. FIG. 19 shows a like linear plot of image values along a radius of FIG. 17 showing substantial radial variation.

Figure 20:
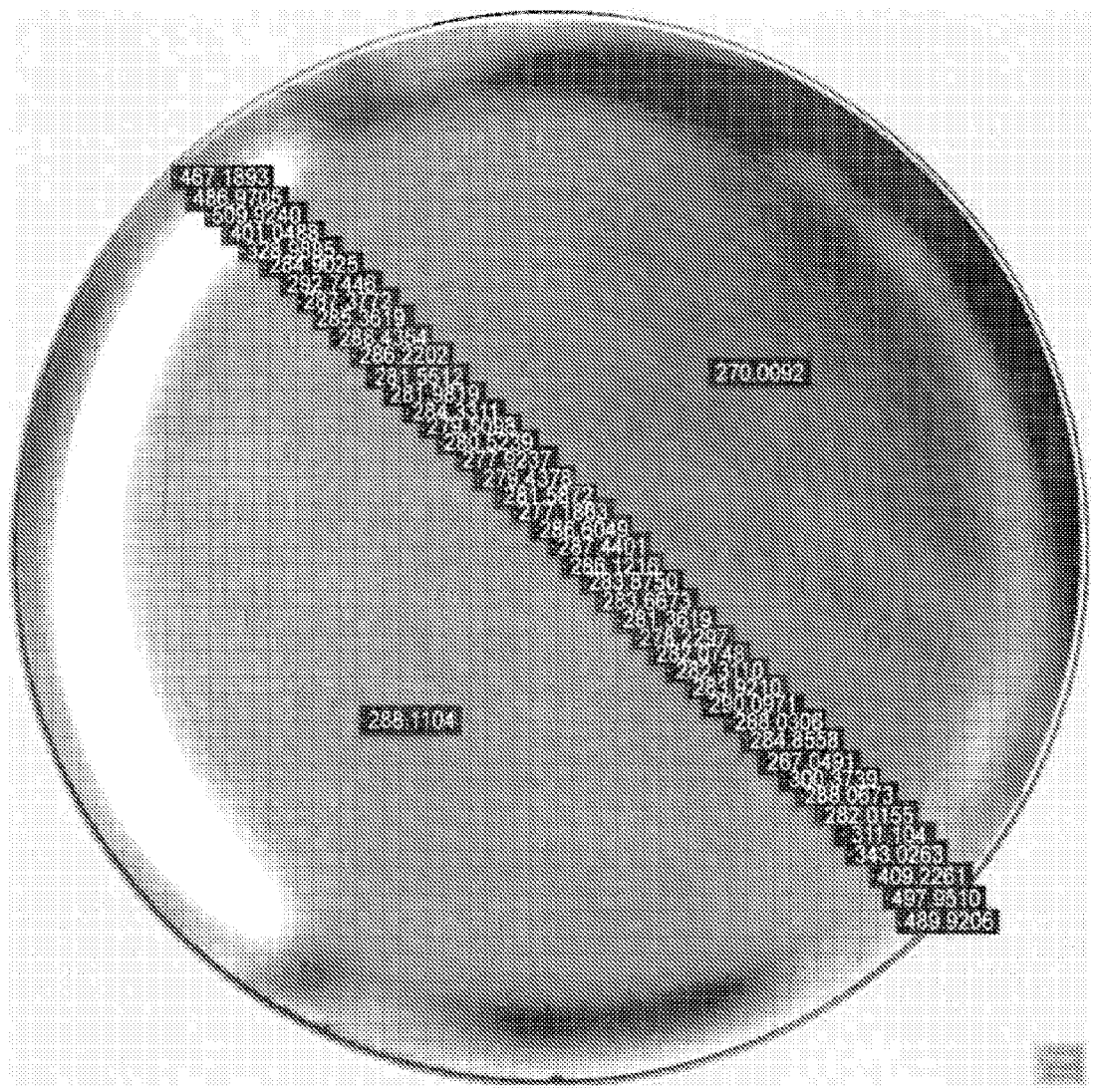
FIG. 20 shows a non-vibrating contact potential difference scanned image of fourth sample wafer with vibrating Kelvin probe measurements identified at data points along a diameter of the wafer.
Figure 21:
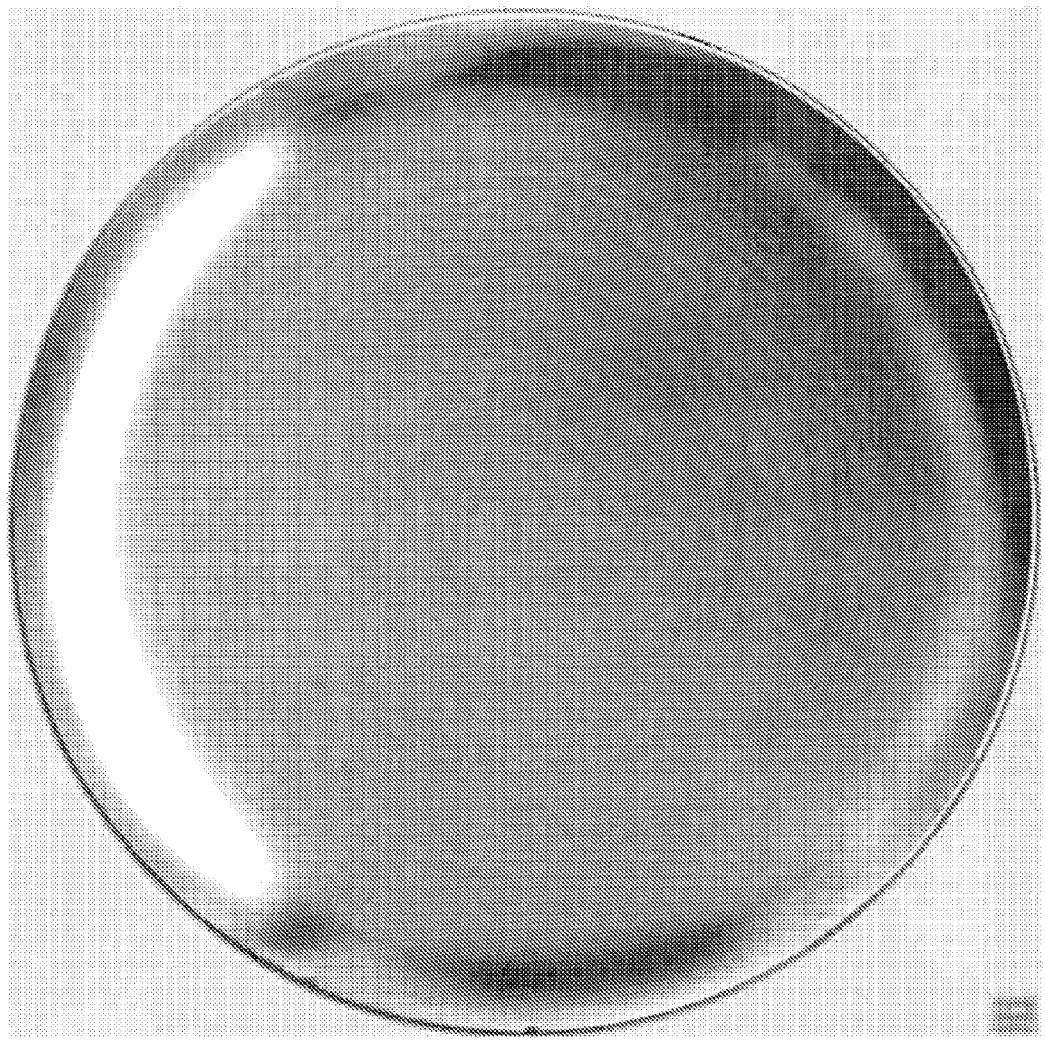
FIG. 21 shows the image from FIG. 20 after integration and scaling (no vibrating probe measurements included), and minimal radial variation of surface potential or work function is visible in this image.
Figure 22:
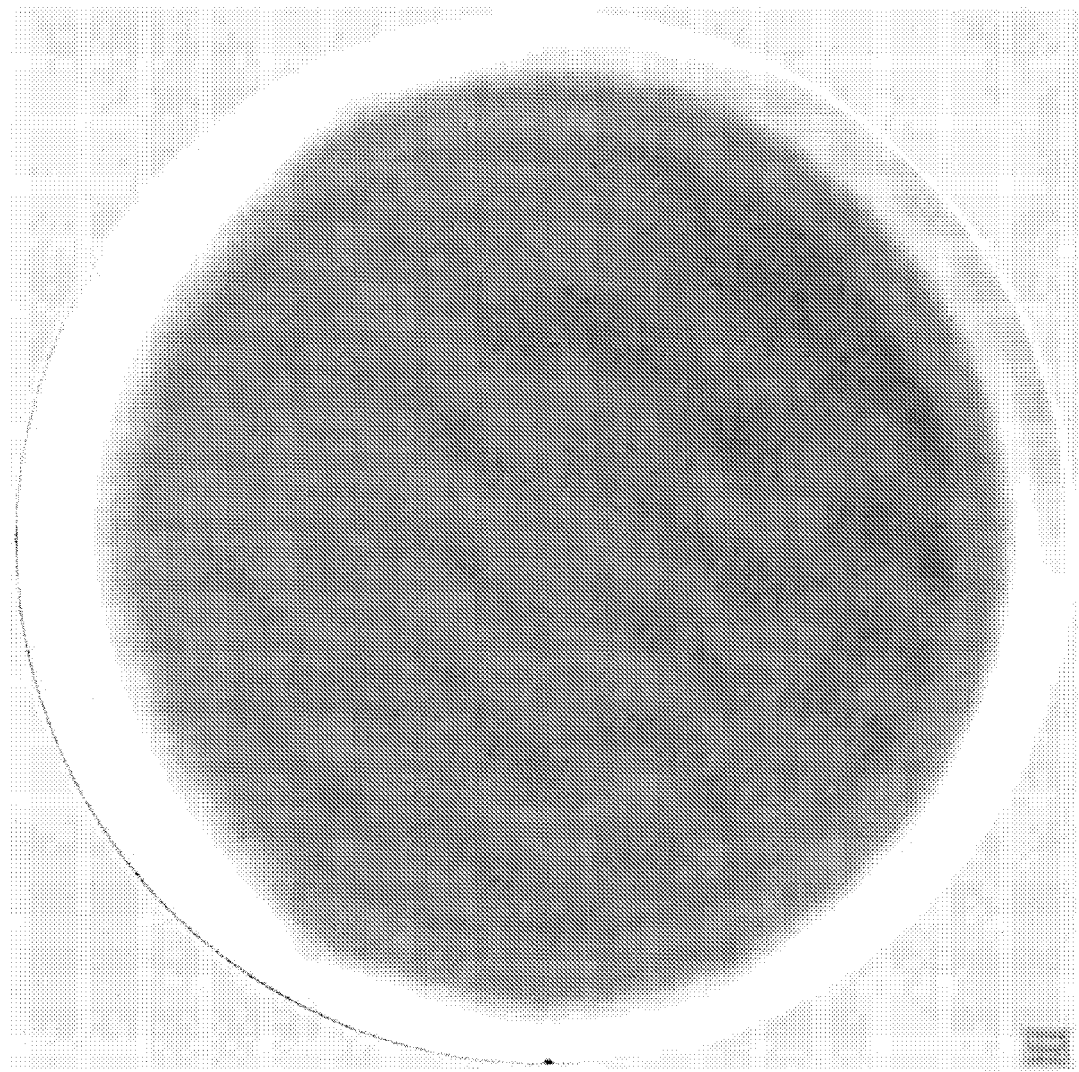
FIG. 22 shows the image for FIG. 20 after offsetting each track based on the vibrating Kelvin probe measurements such that an offset is calculated and applied to each track based on the vibrating Kelvin probe measurement made on the track or on nearby tracks.

FIG. 20 shows the differential non-vibrating contact potential difference image of a fourth sample wafer 105 along with the locations and results of radial vibrating contact potential difference measurements (note labeled data values across a diameter of the fourth wafer 105). FIG. 21 shows data which is representative of relative contact potential difference values, but does not include any information on radial variations in contact potential difference. FIG. 22 shows the same wafer image as FIG. 21 after individual track offsets have been calculated and applied to the integrated and scaled non-vibrating contact potential difference data so that the image data approximately matches the vibrating contact potential difference data at the same points. The integrated, scaled and offset data shows significant radial variation in contact potential difference that is not evident in the differential or integrated image shown in FIGS. 20 and 21. Once again, after these steps have been performed, contact potential difference values can be identified, plotted and/or analyzed along any radius of the fourth wafer 105. It should be noted that the wafer of FIGS. 20-24 underwent a different cleaning process than for the other wafers of FIGS. 7-19. Rather than a single wafer clean and rinse with deonized water, the wafer was cleaned by a conventional, well known plasma processing method.

Figure 23:
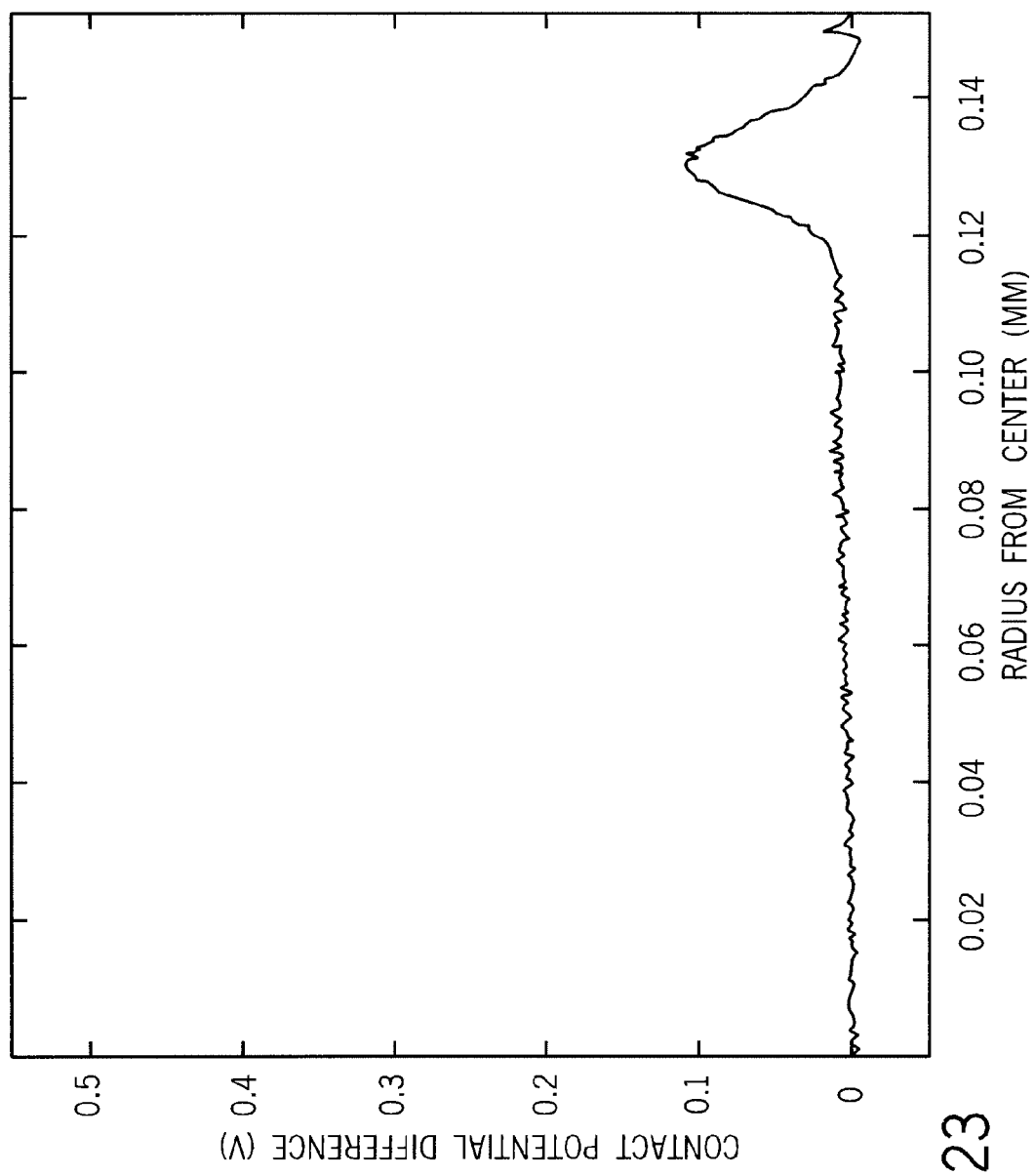
FIG. 23 shows a linear plot from the image values along one radius of the image data of FIG. 21.
Figure 24:
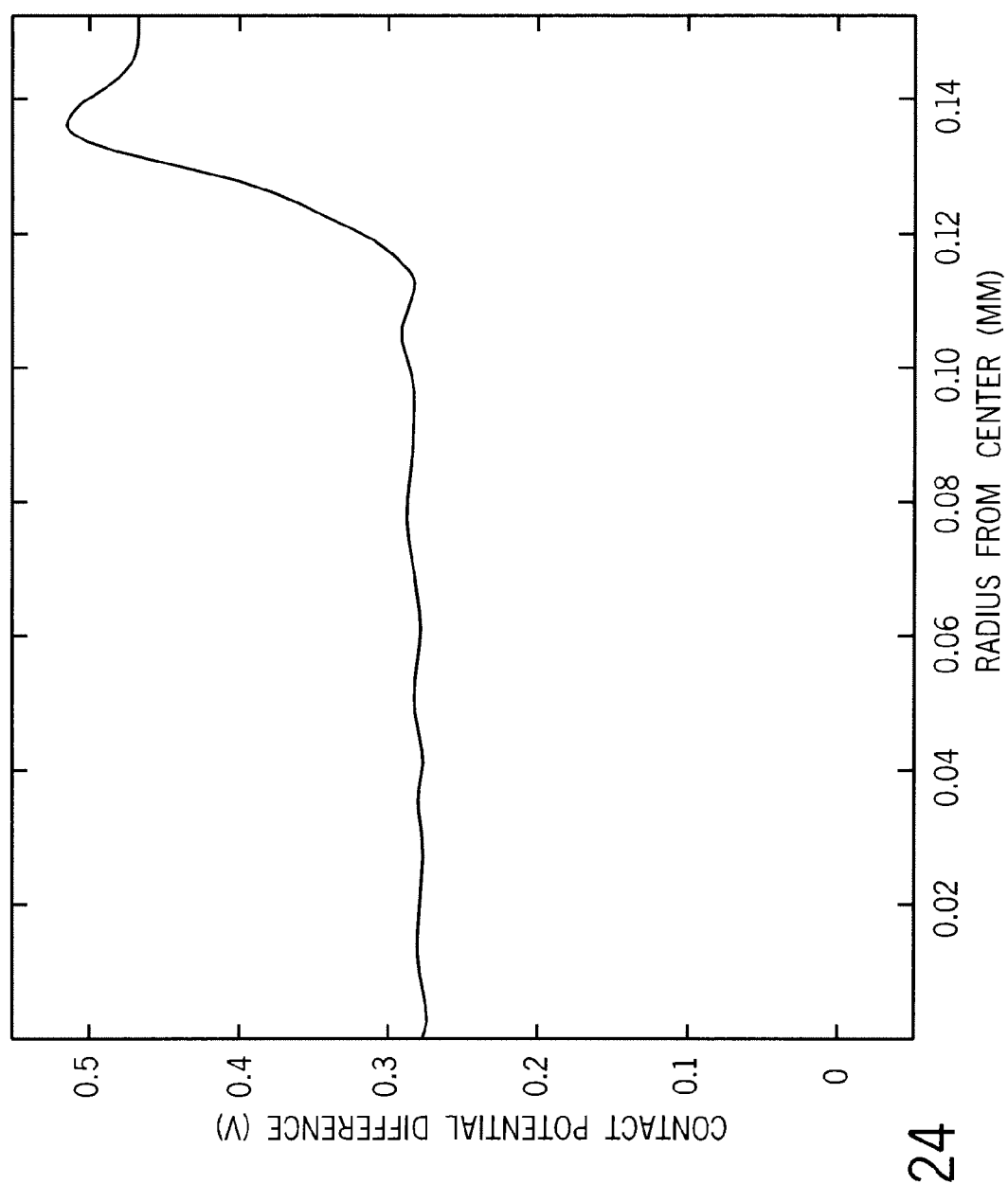
FIG. 24 shows a linear plot of image values taken from the image values along a radius for the wafer image data shown in FIG. 22.

FIG. 23 shows a linear plot of image values along an exemplary radius of FIG. 21 showing minimal radial variations except the different edge portion which are normal artifacts of the method. FIG. 24 shows a like linear plot of image values along a radius of FIG. 22 showing substantial radial variations.

The method of the invention clearly illustrates the dramatic effects that can arise within the confines of "cleaning" or otherwise treating a semiconductor wafer with ostensibly the "same" methodology. The basic method of a clean and rinse with deionized water can be implemented by a number of different conventional cleaning tools which involve the method of applying deionized water to the center of the wafer, ramping up the spin speed of the tool supporting the wafer to distribute the water over the wafer and thereby clean the wafer and then ramping down the spin speed of the support tool. The inspection and analysis method of the invention has enabled identification of a wide range of characteristic differences for the quality of the resulting "cleaned" wafer such that a plurality of different undesirable and desirable cleaning parametric quality states can be identified. For example, given a particular cleaning tool and/or the type of deionized water (conductivity and the like) conditions for treatment can be pre-selected to achieve the desired clean wafer surface. Furthermore, operating conditions of the support tool itself can be optimized, changed or pre-selected to achieve the desired wafer quality result. The sensitivity of the method of the invention therefore enables highly particular characterization of the wafer surface and provides a highly efficient pathway to produce a desired end product wafer for further processing, thereby insuring the desired and/or highest quality and also greatly improved yield. This methodology also allows the characterization of any type of chemical or physical treatment to allow accumulation of correlation data which can be used to reliably produce a predetermined surface quality for a material such as a semiconductor wafer.

There are many alternative mechanical configurations and scanning operations that would accomplish the same result as the embodiments described above. For example, the contact potential difference sensor 101, height sensor 109, and system for vibrating the sensor 104 could all be mounted at fixed locations, and the wafer 105 could be moved and rotated beneath these stationary elements. Instead of stepping from one radius to the next, the contact potential difference sensor 101 could be moved continuously along the wafer 105 radius while the wafer 105 is spinning to create a continuous stream of data that spirals across the whole surface of the wafer 105. Also, instead of the radial scanning operation described above, the non-vibrating contact potential difference sensor 101 could be moved linearly across the wafer 105 in a back-and-forth manner to scan the entire wafer surface 106, or the wafer 105 could be placed on a rotating fixture where the center of rotation is not the center of the wafer 105. Also, multiple non-vibrating and vibrating contact potential difference sensors could be used to acquire multiple measurements simultaneously to reduce the time required to measure a wafer. In addition, some of the steps of the various methods described can readily be interchanged as one of ordinary skill would understand. For example, all scanned and vibrating CPD data can be collected before any subsequent data processing such as integration and scaling. Also, height of the wafer surface can be measured before each vibrating CPD measurement.

The present invention provides an enhanced inspection system that uses both vibrating and non-vibrating contact potential difference sensors to detect surface and sub-surface non-uniformities, including dielectric charging, and a system for processing data from the sensors to accurately quantify and display the contact potential difference at all points on the wafer. This invention is not limited to the inspection of semiconductors or semiconductor wafers and may be used on a wide variety of surfaces.

The foregoing description of embodiments of the present invention have been presented for purposes of illustration and description. It is not intended to be exhaustive or to limit the present invention to the precise form disclosed, and modifications and variations are possible in light of the above teachings or may be acquired from practice of the present invention. The embodiments were chosen and described in order to explain the principles of the present invention and its practical application to enable one skilled in the art to utilize the present invention in various embodiments, and with various modifications, as are suited to the particular use contemplated.

What is claimed is:

1. A method of determining the contact potential difference of a surface of a material to characterize properties of the surface, comprising the steps of:
   providing a surface of a material;
   providing a contact potential difference sensor having a sensor probe tip;
   scanning the surface and contact potential difference sensor relative to one another;
   generating laterally-scanned sensor data representative of changes in contact potential difference between the sensor probe tip and the surface of the material as the sensor probe tip scans laterally relative to the surface of the material;
   processing the laterally-scanned sensor data to provide relative contact potential difference values;
   using a vibrating contact potential difference sensor to make at least one measurement of the absolute contact potential difference of the laterally-scanned surface; and
   using the absolute contact potential difference data to calculate offsets which are added to the relative contact potential values to generate characteristic data which is representative of the contact potential difference between the sensor probe tip and all points on the laterally scanned surface, thereby characterizing properties of the surface of the material.

2. The method as defined in claim 1 wherein the step of processing the laterally scanned sensor data comprises integrating the laterally-scanned sensor data to produce integrated data.

3. The method as defined in claim 2 wherein the step of processing the laterally-scanned sensor data comprises multiplying the integrated data by a scaling factor to convert the laterally-scanned sensor data to the relative contact potential difference values.

4. The method as defined in claim 1 where the lateral scanning motion is generated by rotating the wafer.

5. The method as defined in claim 1 where the laterally scanned sensor data is provided as concentric circular tracks data.

6. The method as defined in claim 1 where the step of making vibrating contact potential difference measurements comprises accumulating data on different tracks.

7. The method as defined in claim 1 further including the step of analyzing the characteristic data to determine variation in surface contact potential difference perpendicular to the direction of travel of the probe tip during scanning.

8. The method as defined in claim 1 further including the step of subjecting the surface of the material to a plurality of different treatments and characterizing the surface of the material to accumulate correlation data associated with each of the different treatments to enable producing predetermined surface qualities for the material.

9. The method as defined in claim 8 wherein the correlation data is further used to pre-program production of a plurality of types of the material having the predetermined surface qualities.

10. The method as defined in claim 8 wherein the different treatments are selected from the group of a cleaning process, a chemical treatment process and a physical treatment process.

11. The method as defined in claim 10 wherein the cleaning process is selected from the group of cleaning by applying a deionized wash and by applying a plasma processing step.

12. A method of determining the contact potential difference of a surface of a material to characterize properties of the surface, comprising the steps of:
   providing a surface of a material;
   providing a contact potential difference sensor having a sensor probe tip;
   scanning the surface and contact potential difference sensor relative to one another;
   generating a first set of laterally-scanned sensor data representative of changes in contact potential difference between the sensor probe tip and the surface of the material as the sensor probe tip scans laterally relative to the surface of the material;
   generating a second set of laterally-scanned sensor data representative of changes in contact potential difference across the surface of the material, the second set of sensor data being generated by moving the contact potential difference sensor perpendicular to the direction of the laterally scanning of the first set of sensor data;
   processing the first and second set of sensor data to determine relative contact potential difference values;
   using a vibrating contact potential difference sensor to make at least one measurement of the absolute contact potential difference of the laterally-scanned surface using a vibrating contact potential difference sensor; and
   using the absolute contact potential difference data to calculate offsets which are added to the integrated, scaled non-vibrating relative contact potential difference data values to generate characteristic data which is representative of the contact potential difference between the sensor probe tip and all points on the laterally scanned surface, thereby characterizing properties of the surface of the material.

13. The method as defined in claim 12 wherein the step of processing the laterally scanned sensor data comprises integrating the laterally-scanned sensor data to produce integrated data.

14. The method as defined in claim 12 wherein the step of processing the laterally-scanned sensor data comprises multiplying the integrated data by a scaling factor to convert the laterally-scanned sensor data to the relative contact potential difference values.

15. A semiconductor wafer prepared for use in an electronic component, at least one of the methods of processing including the steps of:

providing a semiconductor wafer having a surface;
providing a contact potential difference sensor having a sensor probe tip;
scanning the surface of the semiconductor wafer and contact potential difference sensor relative to one another;
generating laterally-scanned sensor data representative of changes in contact potential difference between the sensor probe tip and the surface of the semiconductor wafer as the sensor probe tip scans laterally relative to the surface of the semiconductor wafer;
processing the laterally-scanned sensor data to provide relative contact potential difference values;
using a vibrating contact potential difference sensor to make at least one measurement of the absolute contact potential difference of the laterally-scanned surface; and
using the absolute contact potential difference data to calculate offsets which are added to the relative contact potential values to generate characteristic data which is representative of the contact potential difference between the sensor probe tip and all points on the laterally scanned surface, thereby characterizing properties of the surface of the semiconductor wafer.

16. The method as defined in claim 15 wherein the step of processing the laterally scanned sensor data comprises integrating the laterally-scanned sensor data to produce integrated data.

17. The method as defined in claim 16 wherein the step of processing the laterally-scanned sensor data comprises multiplying the integrated data by a scaling factor to convert the laterally-scanned sensor data to the relative contact potential difference values.

18. The method as defined in claim 15 further including the step of analyzing the characteristic data to determine variation in surface contact potential difference perpendicular to the direction of travel of the probe tip during scanning.

19. The method as defined in claim 15 further including the step of subjecting the surface of the semiconductor wafer to a plurality of different treatments and characterizing the surface of the semiconductor wafer to accumulate correlation data associated with each of the different treatments to enable producing predetermined surface qualities for the semiconductor wafer.

20. The method as defined in claim 19 wherein the correlation data is further used to pre-program production of a plurality of types of the semiconductor wafer having the predetermined surface qualities.

* * * * *